United States Patent
Yuan et al.

(10) Patent No.: US 12,344,853 B2
(45) Date of Patent: *Jul. 1, 2025

(54) bZIP TRANSCRIPTION FACTORS REGULATE CONVERSION OF NICOTINE TO NORNICOTINE AND REDUCE LEVELS OF TOBACCO SPECIFIC (TSNA) PRECURSORS

(71) Applicants: University of Kentucky Research Foundation, Lexington, KY (US); R.J. Reynolds Tobacco Company, Winston-Salem, NC (US)

(72) Inventors: Ling Yuan, Lexington, KY (US); Sanjay K. Singh, Lexington, KY (US); Sitakanta Pattanaik, Lexington, KY (US); Darlene Madeline Lawson, Chapel Hill, NC (US)

(73) Assignees: University of Kentucky Research Foundation, Lexington, KY (US); R. J. Reynolds Tobacco Company, Winston-Salem, NC (US)

( * ) Notice: Subject to any disclaimer, the term of this patent is extended or adjusted under 35 U.S.C. 154(b) by 598 days.

This patent is subject to a terminal disclaimer.

(21) Appl. No.: 17/605,506

(22) PCT Filed: Jun. 5, 2020

(86) PCT No.: PCT/US2020/036426
§ 371 (c)(1),
(2) Date: Oct. 21, 2021

(87) PCT Pub. No.: WO2020/247821
PCT Pub. Date: Dec. 10, 2020

(65) Prior Publication Data
US 2022/0213496 A1    Jul. 7, 2022

Related U.S. Application Data

(60) Provisional application No. 62/857,718, filed on Jun. 5, 2019.

(51) Int. Cl.
| | | |
|---|---|---|
| *C12N 15/82* | (2006.01) | |
| *C07K 14/415* | (2006.01) | |
| *A24B 3/08* | (2006.01) | |

(52) U.S. Cl.
CPC ........ *C12N 15/8243* (2013.01); *C07K 14/415* (2013.01); *C12N 15/8218* (2013.01); *A24B 3/08* (2013.01)

(58) Field of Classification Search
None
See application file for complete search history.

(56) References Cited

U.S. PATENT DOCUMENTS

| | | | |
|---|---|---|---|
| 11,773,401 B2 * | 10/2023 | Yuan ................ | C12N 15/8243 800/278 |
| 2016/0120142 A1 | 5/2016 | Dewey et al. | |
| 2018/0037902 A1 | 2/2018 | Le Lay et al. | |

FOREIGN PATENT DOCUMENTS

| | | |
|---|---|---|
| WO | WO 2008/118394 A1 | 10/2008 |
| WO | WO 2014/031675 A2 | 2/2014 |
| WO | WO 2019/113360 A1 | 6/2019 |

OTHER PUBLICATIONS

Heinekamp T. et al., Mol Genet Genomics (2002) vol. 267, pp. 16-26. (Year: 2002).*
Li et al., 2021 Agronomy, 11:1-17; see p. 13. (Year: 2021).*
Strathmann, A. et al., The Plant Journal (2001) vol. 28, No. 4, pp. 397-408. (Year: 2001).*
Ranawaka, Buddhini (2022) Thesis: The Organisation and Epigenetic Landscape of the Nicotiana Benthamiana Genome; 228 pages, Queensland University of Technology. (Year: 2022).*
XM_009612135 'Predicted: Nicotiana tomentosiformis light-inducible protein CPRF2 (LOC104104130) mRNA; Oct. 19, 2016, pp. 1-2.
Kang, S. et al. 'The *Arabidopsis* bZIP1 Transcription Factor is Involved in Sugar Signaling, Protein Networking, and DNA Binding'. Mol. Plant; Mar. 2010; vol. 3(2); p. 361-373.
Strathmann, A. et al. 'BZI-1 specifically heterodimerises with the tobacco bZIP transcription factors BZI-2, BZI-3/TBZF and BZI-4, and is functionally involved in flower development'. The Plant J. 2001; vol. 28(4); p. 397-408.

* cited by examiner

*Primary Examiner* — Russell Kallis
(74) *Attorney, Agent, or Firm* — Stites & Harbison PLLC; Mandy Wilson Decker

(57) ABSTRACT

A method of decreasing conversion of nicotine to nornicotine is provided herein. The methods includes administering at least one basic region/leucine zipper (bZIP) type transcription factor inhibitor to an organism in need thereof. Also provided herein is a method of decreasing conversion of nicotine to nornicotine including mutating a bZIP type transcription factor binding site on a promoter of a nicotine N-demethylase (NND). Further provided herein is a method of decreasing conversion of nicotine to nornicotine including mutating a plant genome to knockout at least one bZIP type transcription factor.

40 Claims, 19 Drawing Sheets

Specification includes a Sequence Listing.

FIG. 6

SD-Leu-Trp  SD-Leu-Trp-His-Ade

Clockwise from top left – 1, 2, 3, 4

1. AD-NtbZIP1a$^{aa\ 1-144}$ + BD-NtbZIP2a$^{aa\ 1-1455}$
2. AD-NtbZIP1b$^{aa\ 1-144}$ + BD-NtbZIP2a$^{aa\ 1-1455}$
3. AD-NtbZIP2a$^{aa\ 1-455}$ + BD-NtbZIP2a$^{aa\ 1-455}$
4. AD (empty vector) + BD-BD-NtbZIP2a$^{aa\ 1-1455}$ NtbZIP1 (amino acid 1-144)

NtbZIP2 (amino acid 1-455)

SEQUENCE LISTING

```
<160> NUMBER OF SEQ ID NOS: 6

<210> SEQ ID NO 1
<211> LENGTH: 435
<212> TYPE: DNA
<213> ORGANISM: Nicotiana tabacum

<400> SEQUENCE: 1
atggctttga cacagcaacc ggctagttca ggttctgatg gccaacgtta tgccacaaat      60
gacgatagaa aacgaaagag aatggagtcc aaccgtgaat ctgcaaggcg gtcacggatg     120
agaaagcagc agcatttgga ggagttgatg agccaaatga cacagctaca gaatcagaac     180
gttctgtggc gcgagaagat tgatgctgtg ggaagaaact acctcaccct cgatgcggag     240
aacaatgtct tgagggctca aatggcagaa ctgactgaac gcttggattc tctcaattcg     300
ctcactcgtt tctgggctga tgctaatgga ctagctgtgg atatccctga aattcctgac     360
actttgcttg agccctggca gcttccttgc ccaattcaac ccatcactgc ttctgctgat     420
atgtttcagt tttga                                                      435

<210> SEQ ID NO 2
<211> LENGTH: 144
<212> TYPE: PRT
<213> ORGANISM: Nicotiana tabacum

<400> SEQUENCE: 2

Asn Ala Leu Thr Gln Gln Pro Ala Ser Ser Gly Ser Asp Gly Gln Arg
1               5                   10                  15

Tyr Ala Thr Asn Asp Asp Arg Lys Arg Lys Arg Met Glu Ser Asn Arg
```

```
                    20                  25                  30

Glu Ser Ala Arg Arg Ser Arg Met Arg Lys Gln Gln His Leu Glu Glu
            35                  40                  45

Leu Met Ser Gln Met Thr Gln Leu Gln Asn Gln Asn Val Leu Trp Arg
    50                  55                  60

Glu Lys Ile Asp Ala Val Gly Arg Asn Tyr Leu Thr Leu Asp Ala Glu
65                  70                  75                  80

Asn Asn Val Leu Arg Ala Gln Met Ala Glu Leu Thr Glu Arg Leu Asp
                85                  90                  95

Ser Leu Asn Ser Leu Thr Arg Phe Trp Ala Asp Ala Asn Gly Leu Ala
            100                 105                 110

Val Asp Ile Pro Glu Ile Pro Asp Thr Leu Leu Glu Pro Trp Gln Leu
        115                 120                 125

Pro Cys Pro Ile Gln Pro Ile Thr Ala Ser Ala Asp Met Phe Gln Phe
    130                 135                 140

<210> SEQ ID NO 3
<211> LENGTH: 435
<212> TYPE: DNA
<213> ORGANISM: Nicotiana tabacum

<400> SEQUENCE: 3
atggcttcga tacagcaacc agctagttca ggttctgatg ccaacgata tgctatgaac        60 gacgatagaa aacgaaagag aatggagtcc aaccgtgaat ctgcaaggcg gtcacggatg      120
aggaagcagc agcatttgga agagttgatg agccaaatga cacagctaca gaatcagaac      180
gttctgtggc gtgagaagat tgatgctgtg ggaagaaact acctgaccct tgatgcggag      240
aacaatgtcc tgagggctca aatggcagaa ctgactgaac gcttggattc gctcaattcg      300
ctcgctcgtt tctgggctga tgctaatgga ctagctgtgg atatccctga aattccagac      360
actttgcttg agccgtggca gcttccttgc ccaattcaac ccatcactgc ttctgctaat      420
atgtttcagt tttga                                                       435

<210> SEQ ID NO 4
<211> LENGTH: 144
<212> TYPE: PRT
<213> ORGANISM: Nicotiana tabacum

<400> SEQUENCE: 4

Asn Ala Ser Ile Gln Gln Pro Ala Ser Ser Gly Ser Asp Gly Gln Arg
1               5                   10                  15

Tyr Ala Met Asn Asp Asp Arg Lys Arg Lys Met Glu Ser Asn Arg
                20                  25                  30

Glu Ser Ala Arg Arg Ser Arg Met Arg Lys Gln Gln His Leu Glu Glu
            35                  40                  45

Leu Met Ser Gln Met Thr Gln Leu Gln Asn Gln Asn Val Leu Trp Arg
    50                  55                  60

Glu Lys Ile Asp Ala Val Gly Arg Asn Tyr Leu Thr Leu Asp Ala Glu
65                  70                  75                  80

Asn Asn Val Leu Arg Ala Gln Met Ala Glu Leu Thr Glu Arg Leu Asp
                85                  90                  95

Ser Leu Asn Ser Leu Ala Arg Phe Trp Ala Asp Ala Asn Gly Leu Ala
            100                 105                 110

Val Asp Ile Pro Glu Ile Pro Asp Thr Leu Leu Glu Pro Trp Gln Leu
        115                 120                 125
```

-continued

```
Pro Cys Pro Ile Gln Pro Ile Thr Ala Ser Ala Asn Met Phe Gln Phe
    130                 135                 140

<210> SEQ ID NO 5
<211> LENGTH: 455
<212> TYPE: PRT
<213> ORGANISM: Nicotiana tabacum

<400> SEQUENCE: 5

Met Asp Arg Val Phe Ser Val Asp Asp Ile Gly Asp His Phe Trp
1               5                   10                  15

Ser Thr Pro Pro Thr Ala Asp Leu Gly Val Asp Ser Pro Thr Ala Ala
                20                  25                  30

Ala Ala Val Ser Tyr Ser Lys Met Met Asn Arg Ser Ser Ser Glu Trp
            35                  40                  45

Ala Phe Gln Arg Phe Leu Gln Glu Ala Thr Ala Ala Gly Thr Ser Thr
        50                  55                  60

Ser Ser Pro Pro Gln Pro Pro Thr Met Thr Ala Ser Ser Ser Ser Ser
65                  70                  75                  80

Ser His Gln Asn Asp Val Val Glu Ile Lys Asp Glu Asn Leu Ser Ile
                85                  90                  95

Pro Asn Leu Asn Pro Ser Thr Ala Leu Asn Ser Lys Pro Ala Ser Ser
            100                 105                 110

Phe Gly Leu Ala Pro Pro Asn Ile Ala Val Asp Ser Glu Glu Tyr
        115                 120                 125

Gln Ala Phe Leu Lys Ser Gln Leu His Leu Ala Cys Ala Ala Val Ala
    130                 135                 140

Leu Thr Arg Gly Lys Ser Leu Asn Pro Gln Asp Ser Gly Ser Thr Ala
145                 150                 155                 160

His Asp Lys Gly Ser Glu Thr Ala Ser Ala Gln Ser Gly Ser His
                165                 170                 175

Val Ser Thr Leu Gly Lys Cys Tyr Leu Arg Ser Gly Gln Glu Val Ala
            180                 185                 190

Lys Ile Gln Asp Lys Asp Ala Gly Gly Pro Val Gly Ile Pro Ser Leu
        195                 200                 205

Pro Pro Val Gln Lys Lys Pro Val Val Gln Val Arg Ser Thr Thr Ser
    210                 215                 220

Gly Ser Ser Arg Glu Gln Ser Asp Asp Asp Glu Ala Glu Gly Glu Ala
225                 230                 235                 240

Glu Thr Thr Gln Gly Met Asp Pro Ala Asp Ala Lys Arg Val Arg Arg
                245                 250                 255

Met Leu Ser Asn Arg Glu Ser Ala Arg Arg Ser Arg Arg Arg Lys Gln
            260                 265                 270

Ala His Leu Thr Glu Leu Glu Thr Gln Val Ser Gln Leu Arg Val Glu
        275                 280                 285

Asn Ser Ser Leu Leu Lys Arg Leu Thr Asp Ile Ser Gln Lys Tyr Asn
    290                 295                 300

Glu Ala Ala Val Asp Asn Arg Val Leu Lys Ala Asp Val Glu Thr Leu
305                 310                 315                 320

Arg Ala Lys Val Lys Met Ala Glu Glu Thr Val Lys Arg Val Thr Gly
                325                 330                 335

Leu Asn Pro Leu Phe Gln Ala Met Ser Glu Ile Ser Ser Met Val Met
            340                 345                 350

Pro Ser Tyr Ser Gly Ser Pro Ser Asp Thr Ser Ala Asp Ala Ala Val
        355                 360                 365
```

-continued

```
Pro Val Gln Asp Asp Pro Lys His His Tyr Tyr Gln Gln Pro Pro Asn
            370                 375                 380

Asn Leu Met Pro Thr His Asp Pro Arg Ile Gln Asn Gly Met Val Asp
385                 390                 395                 400

Val Pro Pro Ile Glu Asn Val Glu Gln Asn Pro Ala Thr Ala Ala Val
                405                 410                 415

Gly Gly Asn Lys Met Gly Arg Thr Thr Ser Met Gln Arg Val Ala Ser
            420                 425                 430

Leu Glu His Leu Gln Lys Arg Ile Arg Gly Glu Val Ser Ser Cys Gly
            435                 440                 445

Thr Gln Gly Arg Gly Glu Gln
            450                 455

<210> SEQ ID NO 6
<211> LENGTH: 442
<212> TYPE: PRT
<213> ORGANISM: Nicotiana tabacum

<400> SEQUENCE: 6

Met Asp Arg Val Phe Ser Val Asp Asp Ile Gly Asp His Phe Trp
1               5                   10                  15

Ser Thr Pro Pro Thr Ala Asp Leu Gly Val Asp Ser Pro Thr Thr Ala
                20                  25                  30

Thr Ala Ala Ser Tyr Ser Lys Met Met Asn Arg Ser Ser Ser Glu Trp
            35                  40                  45

Ala Phe Gln Arg Phe Leu Gln Glu Ala Thr Ala Ala Gly Thr Ser Thr
        50                  55                  60

Ser Ser His Pro Gln Pro Pro Thr Met Thr Ala Ser Ser Ser Ser Ser
65                  70                  75                  80

Ser His Gln Asn Asp Val Val Glu Ile Lys Asp Glu Asn Leu Ser Thr
                85                  90                  95

Pro Asn Leu Asn Pro Ser Thr Ala Leu Asn Ser Lys Pro Ala Ser Ser
            100                 105                 110

Phe Gly Leu Thr Pro Pro Asn Ile Ala Val Asp Ser Glu Glu Tyr
        115                 120                 125

Gln Ala Phe Leu Lys Ser Gln Leu His Leu Ala Cys Ala Ala Val Ala
    130                 135                 140

Leu Thr Arg Gly Lys Ser Leu Asn Pro Gln Asp Ser Gly Ser Thr Ala
145                 150                 155                 160

His Asp Lys Gly Ser Glu Thr Ala Ser Ala Gln Ser Gly Ser His
                165                 170                 175

Glu Met Ala Lys Ile Gln Asp Lys Asp Ala Gly Gly Pro Val Gly Ile
            180                 185                 190

Pro Ser Leu Pro Pro Val Gln Lys Lys Pro Val Val Gln Val Arg Ser
        195                 200                 205

Thr Thr Ser Gly Ser Ser Arg Glu Gln Ser Asp Asp Glu Ala Glu
    210                 215                 220

Gly Glu Ala Glu Thr Thr Gln Gly Met Asp Pro Ala Asp Ala Lys Arg
225                 230                 235                 240

Val Arg Arg Met Leu Ser Asn Arg Glu Ser Ala Arg Arg Ser Arg Arg
                245                 250                 255

Arg Lys Gln Ala His Leu Thr Glu Leu Glu Thr Gln Val Ser Gln Leu
            260                 265                 270

Arg Val Glu Asn Ser Ser Leu Leu Lys Arg Leu Thr Asp Ile Ser Gln
```

-continued

```
            275                 280                 285
Lys Tyr Asn Glu Ala Ala Val Asp Asn Arg Val Leu Lys Ala Asp Val
        290                 295                 300

Glu Thr Leu Arg Ala Lys Val Lys Met Ala Glu Glu Thr Val Lys Arg
305                 310                 315                 320

Val Thr Gly Leu Asn Pro Leu Phe Gln Ala Met Ser Glu Ile Ser Ser
                325                 330                 335

Met Val Met Pro Ser Tyr Ser Gly Ser Pro Ser Asp Thr Ser Ala Asp
            340                 345                 350

Ala Ala Val Pro Val Gln Asp Asp Pro Lys His His Tyr Tyr Gln Gln
            355                 360                 365

Pro Pro Asn Asn His Met Pro Thr Asn Asp Pro Arg Ile Gln Asn Gly
    370                 375                 380

Met Val Asp Val Pro Pro Ile Glu Asn Val Gln Gln Asn Pro Ala Thr
385                 390                 395                 400

Ala Ala Val Gly Gly Asn Lys Met Gly Arg Thr Ala Ser Met Gln Arg
                405                 410                 415

Val Ala Ser Leu Glu His Leu Gln Lys Arg Ile Arg Gly Glu Ile Ser
            420                 425                 430

Ser Cys Gly Thr Gln Gly Arg Gly Glu Gln
            435                 440
```

bZIP TRANSCRIPTION FACTORS REGULATE CONVERSION OF NICOTINE TO NORNICOTINE AND REDUCE LEVELS OF TOBACCO SPECIFIC (TSNA) PRECURSORS

RELATED APPLICATIONS

This application claims priority from International Patent Application No. PCT/US2020/036426 filed Jun. 5, 2020 which claims the benefit of U.S. Provisional Application Ser. No. 62/857,718 filed Jun. 5, 2019, the entire disclosures of which are incorporated herein by this reference.

SEQUENCE LISTING

The instant application contains a Sequence Listing which has been submitted in ASCII format via EFS-Web and is hereby incorporated by reference in its entirety. The ASCII copy of the Sequence Listing, which was created on Jun. 5, 2020, is named 13177N-2183W2.txt and is 11.8 kilobytes in size.

TECHNICAL FIELD

The present invention relates to articles and methods for regulating conversion of nicotine to nornicotine. In particular, the presently-disclosed subject matter relates to transcription factors for regulating conversion of nicotine to nornicotine and methods of use thereof.

BACKGROUND

*Nicotiana tabacum* (common tobacco) is a natural allotetraploid originated about 200,000 years ago. The maternal S-genome is derived from ancestors of *N. sylvestris* and paternal T-genome from the relatives of *N. tomentosiformis*. Nicotine is the major alkaloid accumulated in most of the cultivated tobacco varieties. During the past decades, significant progress has been made in isolation and characterization structural genes in the nicotine biosynthetic pathway. Jasmonic acid (JA) is a major elicitor of nicotine biosynthesis. JA-responsive transcription factors (TFs) belong to two major families, APETALA2/ETHYLENE RESPONSE FACTORS (AP2/ERFs) and the basic HELIX-LOOP-HELIX (bHLH), and are known to induce the expression of genes encoding key enzymes in the nicotine biosynthetic pathway.

Nicotine and other tropane alkaloids, such as hyoscyamine and scopolamine, are synthesized in roots, and transported through xylem to the leaves. A number transporters have been isolated and characterized for their role in transport and vacuolar sequestration of alkaloids in plants. In tobacco, a number of transporters belonging to the MULTIDRUG and TOXIC COMPOUND ETRUSION (MATE) family, including MATE1/2 and Jasmonate-inducible Alkaloid Transporter (JAT1/2), are involved in transportation and vacuolar sequestration of nicotine. However, TFs involved in regulation of these transporter are not thoroughly studied.

In addition to nicotine, tobacco plants accumulate three other pyridine alkaloids namely, nornicotine, anabasine, and anatabine. Nornicotine is a demethylated nicotine (does not contain a methyl group) that is derived from nicotine by an enzymatic process. It is also a precursor to N-nitrosonornicotine (NNN), which is produced during the curing and processing of tobacco materials. More specifically, during post-harvest processing, nornicotine chemically reacts with the nitrozating agents to form NNN. As NNN belongs to a class of smoking related carcinogens called tobacco specific nitrosamines (TSNA), it is highly desirable to reduce TSNA in tobacco products.

There are two possible ways to reduce TSNA. One is to reduce overall nicotine content; the other is to eliminate conversion of nicotine to nornicotine. Conversion of nicotine to nornicotine is catalyzed by nicotine N-demethylase (NND), a small family of cytochrome P450 enzymes. Three NND genes, CYP82E4v1 (originated from *N. tomentosiformis*), CYP82E5v2 (originated from *N. tomentosiformis*), and CYP82E10 (originated from *N. sylvestris*), have been identified in the conversion of nicotine to nornicotine in tobacco. CYP82E4v1 (E4) plays a major role in nicotine to nornicotine conversion in senescent leaves, while expression of CYP82E10 (E10) is reported to be in the roots and CYP82E5 (E5) functions in both roots and leaves. However, up to this point, transcription factors (TFs) involved in the regulation of nicotine to nornicotine conversion (i.e., transcriptional regulators of E4, 5, and 10 genes) have not been identified. Therefore, although significant progress has been made in biochemical and molecular characterization of these nicotine transporters and enzymes involved in nornicotine biosynthesis, the molecular mechanism underlying the regulation of these genes remains to be elucidated.

Accordingly, there is a need for articles and methods that regulate the conversion of nicotine to nornicotine.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a method of decreasing conversion of nicotine to nornicotine and/or a method of reducing levels of at least one tobacco specific (TSNA) precursor, the method including reducing the activity and/or expression of at least one basic region/leucine zipper (bZIP) type transcription factor in a tobacco plant, a part of a tobacco plant, a tobacco plant cell or cell culture, a tobacco plant seed, or another nicotine containing organism.

Also provided herein, in some embodiments, is use of a reduction in the activity and/or expression of at least one basic region/leucine zipper (bZIP) type transcription factor in a tobacco plant, a part of a tobacco plant, a tobacco plant cell or cell culture, a tobacco plant seed, or another nicotine containing organism for decreasing conversion of nicotine to nornicotine and/or for reducing levels of at least one tobacco specific (TSNA) precursor in the tobacco plant, part of a tobacco plant, tobacco plant seed, or nicotine containing organism.

In some embodiments, the at least one bZIP transcription factor includes C bZIP transcription factor, group S bZIP transcription factor, and combinations thereof. In some embodiments, the at least one bZIP transcription factor includes NtbZIP1a, NtbZIP1b, NtbZIP2a, NtbZIP2b, and combinations thereof. In some embodiments, the at least one bZIP transcription factor comprises NtbZIP1a and NtbZIP1b. In some embodiments, the at least one bZIP transcription factor comprises NtbZIP2a and NtbZIP2b. In some embodiments, the at least one bZIP transcription factor comprises NtbZIP1a, NtbZIP1b, NtbZIP2a, and NtbZIP2b.

In some embodiments, the at least one bZIP transcription factor comprises an amino acid molecule having at least 90%, 95%, 97%, 98%, 99%, or 100% identity to an amino acid encoded by SEQ ID NO: 1; the amino acid of SEQ ID NO: 2; the amino acid encoded by SEQ ID NO: 3; the amino acid of SEQ ID NO: 4; the amino acid of SEQ ID NO: 5; and the amino acid of SEQ ID NO: 6. In one embodiment, the at least one bZIP transcription factor comprises an amino acid molecule having at least 90%, 95%, 97%, 98%, 99%, or 100% identity to an amino acid encoded by SEQ ID NO: 1 or the amino acid of SEQ ID NO: 2; and an amino acid molecule having at least 90%, 95%, 97%, 98%, 99%, or 100% identity to an amino acid encoded by SEQ ID NO: 3 or the amino acid of SEQ ID NO: 4. In one embodiment, the at least one bZIP transcription factor comprises an amino acid molecule having at least 90%, 95%, 97%, 98%, 99%, or 100% identity to the amino acid of SEQ ID NO: 5; and an amino acid molecule having at least 90%, 95%, 97%, 98%, 99%, or 100% identity to the amino acid of SEQ ID NO: 6. In one embodiment, the at least one bZIP transcription factor comprises an amino acid molecule having at least 90%, 95%, 97%, 98%, 99%, or 100% identity to an amino acid encoded by SEQ ID NO: 1 or the amino acid of SEQ ID NO: 2; an amino acid molecule having at least 90%, 95%, 97%, 98%, 99%, or 100% identity to an amino acid encoded by SEQ ID NO: 3 or the amino acid of SEQ ID NO: 4; an amino acid molecule having at least 90%, 95%, 97%, 98%, 99%, or 100% identity to the amino acid of SEQ ID NO: 5; and/or an amino acid molecule having at least 90%, 95%, 97%, 98%, 99%, or 100% identity to the amino acid of SEQ ID NO: 6.

In some embodiments, reducing the activity and/or expression of the at least one bZIP type transcription factor includes: mutating the bZIP type transcription factor, such as providing a mutation in a binding site of the bZIP type transcription factor; using a bZIP type transcription factor inhibitor; or using a gene silencing technique, such as RNAi. In some embodiments, the bZIP transcription factor inhibitor includes antisense oligonucleotides, miRNA, siRNA, locked nucleic acid (LNA) nucleotides, or a combination thereof.

In some embodiments, mutating the bZIP type transcription factor comprises mutating the binding site on a promoter of a nicotine N-demethylase (NND). In one embodiment, the NND is includes CYP82E4v1, CYP82E5v2, or CYP82E10. In another embodiment, the NND is CYP82E4v1 and the bZIP binding site on the promoter of CYP82E4v1 is an A/G box with a pre-mutated sequence of TACGTC. In another embodiment, the mutated binding site has the sequence TGCGTC. In another embodiment, the mutated binding site is formed by site-directed mutagenesis.

In some embodiments, mutating the bZIP type transcription factor comprises mutating a plant genome to knockout at least one basic region/leucine zipper (bZIP) type transcription factor. In one embodiment, the at least one bZIP transcription factor includes C bZIP transcription factor, group S bZIP transcription factor, or combinations thereof. In one embodiment, the at least one bZIP transcription factor includes NtbZIP1a, NtbZIP1b, NtbZIP2a, NtbZIP2b, or combinations thereof. In one embodiment, the at least one bZIP transcription factor comprises an amino acid sequence having at least 90%, 95%, 97%, 98%, 99%, or 100% identity to an amino acid encoded by SEQ ID NO: 1 or the amino acid of SEQ ID NO: 2; an amino acid encoded by SEQ ID NO: 3 or the amino acid of SEQ ID NO: 4; the amino acid of SEQ ID NO: 5; or the amino acid of SEQ ID NO: 6.

Also provided herein, in some embodiments, is an isolated nucleic acid molecule comprising a nucleic acid sequence having at least 90%, 95%, 97%, 98%, 99%, or 100% identity to the sequence of SEQ ID NO: 1 or SEQ ID NO: 3; a nucleic acid sequence encoding a sequence having at least 90%, 95%, 97%, 98%, 99%, or 100% identity to the sequence of SEQ ID NOs: 2, 4, 5, or 6; or combinations thereof.

Also provided herein, in some embodiments, is an isolated nucleic acid molecule encoding a bZIP type transcription factor having at least one mutation. In one embodiment, the mutation is in the binding site on a promoter of a nicotine N-demethylase (NND). In another embodiment, the NND includes CYP82E4v1, CYP82E5v2, or CYP82E10. In another embodiment, the NND is CYP82E4v1 and the bZIP binding site on the promoter of CYP82E4v1 is an A/G box with a pre-mutated sequence of TACGTC. In another embodiment, the mutated binding site has the sequence TGCGTC. In some embodiments, the bZIP transcription factor comprises NtbZIP1a, NtbZIP1b, NtbZIP2a, NtbZIP2b, or combinations thereof. In some embodiments, the bZIP transcription factor comprises a nucleic acid sequence having the sequence of SEQ ID NO: 1 or SEQ ID NO: 3; a nucleic acid sequence encoding a sequence having the sequence of SEQ ID NOs: 2, 4, 5, or 6; or combinations thereof.

Also provided herein, in some embodiments, is a construct or vector comprising a nucleic acid molecule described herein.

Also provided herein, in some embodiments, is a tobacco plant cell a) comprising an exogenous gene comprising the nucleic acid molecule described herein; b) comprising a construct or vector described herein; c) obtained or obtainable by the method described herein; and/or d) obtained by a mutation to reduce the activity and/or expression of at least one bZIP type transcription factor or to knockout at least one bZIP type transcription factor.

Also provided herein, in some embodiments, is use of a tobacco cell described herein for the production of a tobacco industry product.

Also provided herein, in some embodiments, is a tobacco cell culture or plant a) comprising a plant cell described herein; b) which has been modified to achieve a decrease in conversion of nicotine to nornicotine and/or reduction in levels of at least one tobacco specific (TSNA) precursor of said culture or plant compared with that of an unmodified culture or plant; c) comprising a construct or vector described herein.

Also provided herein, in some embodiments, is a plant propagation material or a plant extract obtainable from a plant described herein or of a portion of said plant. In one embodiment, the plant propagation material is a plant seed.

Also provided herein, in some embodiments, is the use of a tobacco plant described herein to breed a tobacco plant. In some embodiments, the use of the tobacco plant described herein is for production of a tobacco industry product. In some embodiments, the use of the tobacco plant described herein is to grow a crop. In some embodiments, the use of the tobacco plant described herein is to produce a processed tobacco leaf. In one embodiment, the processed tobacco leaf is a cured tobacco leaf.

Also provided herein, in some embodiments, is a harvested leaf of a tobacco plant described herein. In some embodiments, the harvested leaf is a cut harvested leaf.

Also provided herein, in some embodiments, is a processed tobacco leaf a) comprising a plant cell described herein; b) obtainable from processing a tobacco plant described herein; c) obtainable from a plant propagated from a plant propagation material described herein; and/or d) obtainable by processing a harvested leaf described herein. In some embodiments, the processed tobacco leaf is a non-viable processed tobacco leaf. In some embodiments, the plant or leaf is processed by curing, fermentation, pasteurizing or combinations thereof. In some embodiments, the processed tobacco leaf is a cut processed tobacco leaf.

Also provided herein, in some embodiments, is a cured tobacco material made from a plant, a part thereof, an extract thereof, or a cell culture described herein.

Also provided herein, in some embodiments, is a tobacco blend comprising the cured tobacco material described herein.

Also provided herein, in some embodiments, is a tobacco industry product comprising a) prepared from a tobacco plant described herein or a part thereof; b) prepared from a tobacco plant or a part thereof (preferably the leaves harvested from the plant) obtained or obtainable by the methods described herein; c) prepared from the plant (preferably the leaves) propagated from a plant propagation material described herein; d) prepared from a harvested leaf described herein; e) prepared from a processed leaf described herein; f) prepared from or comprising a plant extract obtained from a modified plant described herein; g) a cured tobacco material described herein; and/or h) a tobacco blend described herein. In some embodiments, the tobacco industry product is a smoking article. In some embodiments, the tobacco industry product is a smokeless tobacco product. In some embodiments, the tobacco product is a non-combustible aerosol provision system such as a tobacco heating device, e.g. an aerosol-generating device.

Also provided herein, in some embodiments, is a combustible smoking article, non-combustible aerosol provisioning system, smokeless tobacco product, or tobacco heating comprising a plant or a portion thereof from the species *Nicotiana tabacum* or *Nicotiana rustica* described herein or an extract thereof or a tobacco cell culture described herein or a cured tobacco material described herein or a tobacco blend described herein.

Also provided herein, in some embodiments, is the use of a nucleotide sequence of at least one gene encoding a bZIP type transcription factor having at least one mutation, wherein the sequence of the bZIP type transcription factor includes a sequence encoded by a nucleic acid sequence comprising a nucleic acid sequence having at least one mutation relative to the sequence of SEQ ID NO: 1 or SEQ ID NO: 3; a sequence having at least one mutation relative to the sequence of SEQ ID NOs: 2, 4, 5, or 6; or combinations thereof. In some embodiments, the sequence is used to select a plant having reduced content of tobacco specific nitrosamine (TSNA) or a precursor of a TSNA.

Further features and advantages of the presently-disclosed subject matter will become evident to those of ordinary skill in the art after a study of the description, figures, and non-limiting examples in this document.

BRIEF DESCRIPTION OF THE SEQUENCE LISTING

The instant application contains a Sequence Listing which is attached hereto.

SEQ ID NO: 1 is a nucleotide sequence encoding NtbZIP1a.
SEQ ID NO: 2 is the amino acid sequence of NtbZIP1a.
SEQ ID NO: 3 is a nucleotide sequence encoding NtbZIP1b.
SEQ ID NO: 4 is the amino acid sequence of NtbZIP1b.
SEQ ID NO: 5 is the amino acid sequence of NtbZIP2a.
SEQ ID NO: 6 is the amino acid sequence of NtbZIP2b.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein:

FIG. 6 shows an image comparing the nucleotide and amino acid sequences of NtbZIP1a and 1b.

Figure 1:
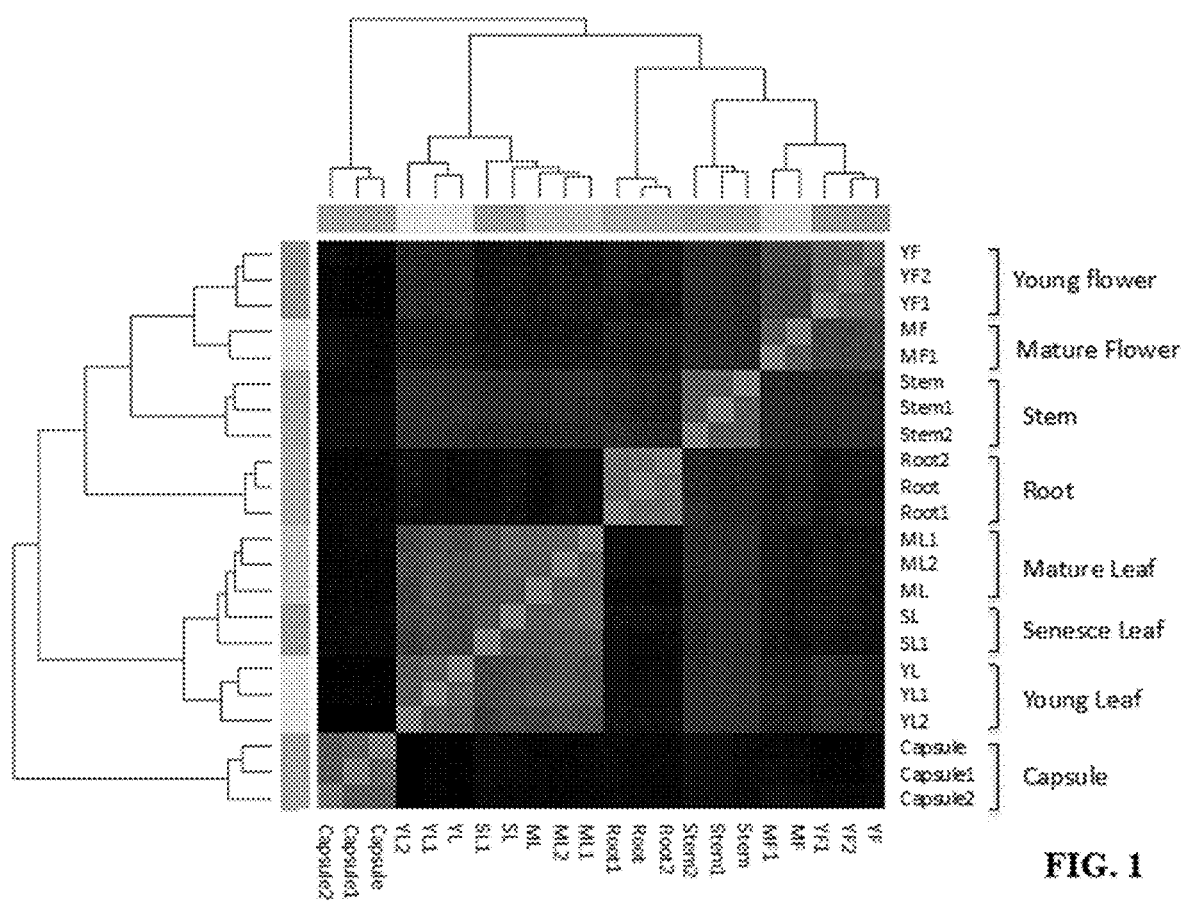
FIG. 1 shows a graph illustrating hierarchical cluster analysis of the transcriptome data of eight different tobacco tissues. Each tissue forms a distinct cluster based on the expression.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

Definitions

Unless defined otherwise, all technical and scientific terms used herein have the same meaning as commonly understood by one of ordinary skill in the art to which the disclosure belongs. Any methods and materials similar to or equivalent to those described herein can be used in the practice or testing of the present disclosure, including the methods and materials are described below.

Following long-standing patent law convention, the terms "a," "an," and "the" refer to "one or more" when used in this application, including the claims. Thus, for example, reference to "a cell" includes a plurality of cells, and so forth.

The terms "comprising," "including," and "having" are intended to be inclusive and mean that there may be additional elements other than the listed elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration, percentage, or the like is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, in some embodiments ±0.1% from the specified amount, and in some embodiments ±0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Certain sequences are described herein with reference to sequence "identity." Sequence identity comparisons can be conducted by eye, or more usually, with the aid of readily available sequence comparison programs. These commercially available computer programs can calculate % identity between two or more sequences.

% identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % identity when a global alignment is performed. Consequently, most sequence comparison methods are designed to produce optimal alignments that take into consideration possible insertions and deletions without penalizing unduly the overall identity score. This is achieved by inserting "gaps" in the sequence alignment to try to maximize local identity.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimized alignments with fewer gaps. Most alignment programs allow the gap penalties to be modified. However, it is preferred to use the default values when using such software for sequence comparisons.

Calculation of maximum % identity therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al 1990 J.

Mol. Biol. 403-410) and AlignX for example. At least BLAST, BLAST 2 and FASTA are available for offline and online searching (see Ausubel et al 1999, pages 7-58 to 7-60).

Although the final % identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage identities may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % sequence identity. The software typically does this as part of the sequence comparison and generates a numerical result.

Should Gap Penalties be used when determining sequence identity, the following parameters may be used for pairwise alignment:

| FOR BLAST | | |
| --- | --- | --- |
| GAP OPEN | | 0 |
| GAP EXTENSION | | 0 |
| FOR CLUSTAL | DNA | PROTEIN |
| WORD SIZE | 2 | 1  K triple |
| GAP PENALTY | 15 | 10 |
| GAP EXTENSION | 6.66 | 0.1 |

In one embodiment, BLAST may be used with the gap penalty and gap extension set as defined above.

In one embodiment, CLUSTAL may be used with the gap penalty and gap extension set as defined above.

In some embodiments the gap penalties used for BLAST or CLUSTAL alignment may be different to those detailed above. The skilled person will appreciate that the standard parameters for performing BLAST and CLUSTAL alignments may change periodically and will be able to select appropriate parameters based on the standard parameters detailed for BLAST or CLUSTAL alignment algorithms at the time.

Suitably, the degree of identity with regard to a nucleotide sequence or an amino acid sequence is determined over at least 20 contiguous nucleotides/amino acids, preferably over at least 30 contiguous nucleotides/amino acids, preferably over at least 40 contiguous nucleotides/amino acids, preferably over at least 50 contiguous nucleotides/amino acids, preferably over at least 60 contiguous nucleotides/amino acids, preferably over at least 100 contiguous nucleotides/amino acids.

Suitably, the degree of identity with regard to a nucleotide sequence or the amino acid sequence may be determined over the whole sequence.

The sequences may also have deletions, insertions or substitutions of amino acid residues which produce a silent change and result in a functionally equivalent substance.

Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
| --- | --- | --- |
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilized for the purpose of the discussion above (relating to homologous or non-homologous substitution), to indicate the hydrophobic nature of the derivative whereas # has been utilized to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, *Trends Biotechnol*. (1995) 13(4), 132-134.

The present invention also encompasses sequences that are complementary to the nucleic acid sequences of the present invention or sequences that are capable of hybridizing either to the sequences of the present invention or to sequences that are complementary thereto.

The term "hybridization" as used herein shall include "the process by which a strand of nucleic acid joins with a complementary strand through base pairing" as well as the process of amplification as carried out in polymerase chain reaction (PCR) technologies.

The present invention also relates to nucleotide sequences that can hybridize to the nucleotide sequences of the present invention (including complementary sequences of those presented herein).

Preferably, hybridization is determined under stringent conditions (e.g. 50° C. and 0.2×SSC {1×SSC=0.15 M NaCl, 0.015 M $Na_3$ citrate pH 7.0}).

More preferably, hybridization is determined under high stringent conditions (e.g. 65° C. and 0.1×SSC {1×SSC=0.15 M NaCl, 0.015 M $Na_3$ citrate pH 7.0}).

The term "commercially desirable traits" will include traits such as yield, quality (e.g. leaf quality, suitably cured leaf quality), abiotic (for instance drought) stress tolerance, herbicide tolerance and/or biotic (for instance insect, bacteria or fungus) stress tolerance and/or disease tolerance.

Leaf quality may be measured based on color, texture and aroma of the cured leaf, for example according to United States Department of Agriculture (USDA) grades and standards.

Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast.

Leaf grade can be determined using standard methods known in the art, for example, using
an Official Standard Grade published by the Agricultural Marketing Service of the US
Department of Agriculture (7 U.S.C. § 511). See, e.g., Official Standard Grades for Burley
Tobacco (U.S. Type 31 and Foreign Type 93), effective Nov. 5, 1990 (55 F.R. 40645);
Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania SeedleafTobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida ShadeGrown Cigar-Wrapper Tobacco (U.S. Type 62), Effective April 1971. A USDA grade index value can be determined according to an industry accepted grade index. See, e.g., Bowman et al, Tobacco Science, 32:39-40(1988); Legacy Tobacco Document Library (Bates Document #523267826-523267833, Jul. 1, 1988, Memorandum on the Proposed Burley Tobacco Grade Index); and Miller et al., 1990, Tobacco Intern., 192:55-57 (all foregoing references are incorporated herein in their entirety).

In one aspect, a USDA grade index is a 0-100 numerical representation of federal grade received and is a weighted average of all stalk positions. A higher grade index indicates higher quality. Alternatively, leaf grade may be determined via hyper-spectral imaging. See e.g., WO 2011/027315 (which is incorporated herein by reference).

In one embodiment, a tobacco plant of the present invention provides tobacco of commercially acceptable grade.

Suitably, the tobacco plant of the present invention provides cured tobacco of commercially acceptable grade.

In one embodiment, a tobacco plant of the present invention is capable of producing leaves having a USDA grade index value of at least about 70% of the USDA grade index value of leaves of a comparable plant when grown in similar growth conditions. Suitably, tobacco plants disclosed herein may be capable of producing leaves having a USDA grade index value of at least about 65%, at least about 70%, at least about 75%, at least about 80%, at least about 85%, at least about 90%, at least about 95%, or at least about 98% of the USDA grade index value of a control plant when grown in similar growth conditions. Suitably, tobacco plants disclosed herein may be capable of producing leaves having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of a comparable plant.

In one aspect, the tobacco plant of the present invention is capable of producing leaves having a USDA grade index value of at least 50. Suitably, tobacco plants disclosed herein may be capable of producing leaves having a USDA grade index value of 55 or more, 60 or more, 65 or more, 70 or more, 75 or more, 80 or more, 85 or more, 90 or more, and 95 or more.

Unless specified otherwise, used herein, tobacco yield refers to cured leaf yield which is calculated based on the weight of cured tobacco leaves per acre under standard field conditions following standard agronomic and curing practice.

In one aspect, a tobacco plant of the present invention has a yield between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the yield of a comparable plant when grown in similar field conditions.

In another aspect, the yield of a tobacco plant of the present invention is approximately 1.5, 1.6, 1.7, 1.8, 1.9, 2.0, 2.1, 2.2, 2.3, 2.4, 2.5, 2.6, 2.7, 2.8, 2.9, or 3.0 times of the yield of the a comparable plant when grown in similar field conditions.

In another aspect, the yield of a tobacco plant of the present invention is comparable to the yield of a cured comparable plant when grown in similar field conditions.

In one aspect, a tobacco plant of the present invention provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre.

In another aspect, a tobacco plant of the present invention provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre.

In a further aspect, a tobacco plant of the present invention provides a yield selected from the group consisting of about between 1200 and 3500, between 1200 and 3400, between 1200 and 3300, between 1200 and 3200, between 1200 and 3100, between 1200 and 3000, between 1200 and 2900, between 1200 and 2800, between 1200 and 2700, between 1200 and 2600, between 1200 and 2500, between 1200 and 2400, between 1200 and 2300, between 1200 and 2200, between 1200 and 2100, between 1200 and 2000, between 1200 and 1900, between 1200 and 1800, between 1200 and 1700, between 1200 and 1600, between 1200 and 1500, and between 1200 and 1400 lbs/acre.

The term "tobacco plant" as used herein refers to a plant in the genus *Nicotiana* that is used in the production of tobacco industry products. Non-limiting examples of suitable tobacco plants include *N. tabacum* and *N. rustica* (for example, LA B21, LN KY171, Tl 1406, Basma, Galpao, Perique, Beinhart 1000-1, and Petico).

Thus, in one embodiment a tobacco plant does include *Nicotiana plumbaginifolia*.

The tobacco material can be derived from varieties of *Nicotiana tabacum* species, commonly known as Burley varieties, flue or bright varieties, dark varieties and oriental/Turkish varieties. In some embodiments, the tobacco material is derived from a Burley, Virginia, flue-cured, air-cured, fire-cured, Oriental, or a dark tobacco plant. The tobacco plant may be selected from Maryland tobacco, rare tobacco, specialty tobacco, expanded tobacco or the like.

The use of tobacco cultivars and elite tobacco cultivars is also contemplated herein. The tobacco plant for use herein may therefore be a tobacco variety or elite tobacco cultivar.

Particularly useful *Nicotiana tabacum* varieties include Burley type, dark type, flue-cured type, and Oriental type tobaccos.

The tobacco plant may be, for example, selected from one or more of the following varieties: *N. tabacum* AA 37-1, *N. tabacum* B 13P, *N. tabacum* Xanthi (Mitchell-Mor), *N. tabacum* KT D #3 Hybrid 107, *N. tabacum* Bel-W3, *N. tabacum* 79-615, *N. tabacum* Samsun Holmes NN, F4 from cross *N. tabacum* BU21×*N. tabacum* Hoja Parado, line 97, *N. tabacum* KTRDC #2 Hybrid 49, *N. tabacum* KTRDC #4 Hybrid 110, *N. tabacum* Burley 21, *N. tabacum* PM016, *N. tabacum* KTRDC #5 KY 160 SI, *N. tabacum* KTRDC #7 FCA, *N. tabacum* KTRDC #6 TN 86 SI, *N. tabacum* PM021, *N. tabacum* K 149, *N. tabacum* K 326, *N. tabacum* K 346, *N. tabacum* K 358, *N. tabacum* K 394, *N. tabacum* K 399, *N. tabacum* K 730, *N. tabacum* KY 10, *N. tabacum* KY 14, *N. tabacum* KY 160, *N. tabacum* KY 17, *N. tabacum* KY 8959, *N. tabacum* KY 9, *N. tabacum* KY 907, *N. tabacum* MD 609, *N. tabacum* McNair 373, *N. tabacum* NC 2000, *N. tabacum* PG 01, *N. tabacum* PG 04, *N. tabacum* P01, *N. tabacum* P02, *N. tabacum* P03, *N. tabacum* RG 11, *N. tabacum* RG 17, *N. tabacum* RG 8, *N. tabacum* Speight G-28, *N. tabacum* TN 86, *N. tabacum* TN 90, *N. tabacum* VA 509, *N. tabacum* AS44, *N. tabacum* Banket A1, *N. tabacum* Basma Drama B84/31, *N. tabacum* Basma I Zichna ZP4/B, *N. tabacum* Basma Xanthi BX 2A, *N. tabacum* Batek, *N. tabacum* Besuki Jember, *N. tabacum* C104, *N. tabacum* Coker 319, *N. tabacum* Coker 347, *N. tabacum* Criollo Misionero, *N. tabacum* PM092, *N. tabacum* Delcrest, *N. tabacum* Djebel 81, *N. tabacum* DVH 405, *N. tabacum* Galpao Comum, *N. tabacum* HBO4P, *N. tabacum* Hicks Broadleaf, *N. tabacum* Kabakulak Elassona, *N. tabacum* PM102, *N. tabacum* Kutsage El, *N. tabacum* KY 14xL8, *N. tabacum* KY 171, *N. tabacum* LA BU 21, *N. tabacum* McNair 944, *N. tabacum* NC 2326, *N. tabacum* NC 71, *N. tabacum* NC 297, *N. tabacum* NC 3, *N. tabacum* PVH 03, *N. tabacum* PVH 09, *N. tabacum* PVH 19, *N. tabacum* PVH 21 10, *N. tabacum* Red Russian, *N. tabacum* Samsun, *N. tabacum* Saplak, *N. tabacum* Simmaba, *N. tabacum* Talgar 28, *N. tabacum* PM132, *N. tabacum* Wislica, *N. tabacum* Yayaldag, *N. tabacum* NC 4, *N. tabacum* TR Madole, *N. tabacum* Prilep HC-72, *N. tabacum* Prilep P23, *N. tabacum* Prilep PB 156/1, *N. tabacum* Prilep P12-2/1, *N. tabacum* Yaka JK-48, *N. tabacum* Yaka JB 125/3, *N. tabacum* TI-1068, *N. tabacum* KDH-960, *N. tabacum* TI-1070, *N. tabacum* TW136, *N. tabacum* PM204, *N. tabacum* PM205, *N. tabacum* Basma, *N. tabacum* TKF 4028, *N. tabacum* L8, *N. tabacum* TKF 2002, *N. tabacum* TN90, *N. tabacum* GR141, *N. tabacum* Basma xanthi, *N. tabacum* GR149, *N. tabacum* GR153, and *N. tabacum* Petit Havana.

Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14xL8 LC, Little Crittenden, McNair 373, McNair 944, msKY 14xL8, Narrow Leaf Madole, Narrow Leaf Madole LC, NBH 98, N-126, N-777LC, N-7371 LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC 'Periq'e' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, Tl 1406, Tl 1269, TN 86, TN86LC, TN 90, TN 97, TN97LC, TN D94, TN D950, TR (Tom Rosson) Madole, VA 309, VA359, AA 37-1, B 13P, Xanthi (Mitchell-Mor), Bel-W3, 79-615, Samsun Holmes NN, KTRDC number 2 Hybrid 49, Burley 21, KY 8959, KY 9, MD 609, PG 01, PG 04, P01, P02, P03, RG 11, RG 8, VA 509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpao Comum, HBO4P, Hicks Broadleaf, Kabakulak Elassona, Kutsage E1, LA BU 21, NC 2326, NC 297, PVH 21 10, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, Tl-1070, TW136, Basma, TKF 4028, L8, TKF 2002, GR141, Basma xanthi, GR149, GR153, Petit Havana. Low converter subvarieties of the above, even if not specifically identified herein, are also contemplated.

The tobacco plant can be, for example, a Burley type tobacco plant, suitably a Burley PH2517.

The plant propagation material can be, for example, obtainable from a tobacco plant of the invention.

A "plant propagation material" as used herein refers to any plant matter taken from a plant from which further plants may be produced. Suitably, a plant propagation material may be selected from a seed, plant calli and plant clumps.

Suitably the plant propagation material may be a seed. Suitably, a plant propagation material may be plant calli. Suitably the plant propagation material may be plant clumps.

The cell (e.g. tobacco cell), tobacco plant and/or plant propagation material can be, for example, obtainable (e.g. obtained) by a method according to the invention.

The term "processed tobacco leaf" as used herein refers to a tobacco leaf that has undergone one or more processing steps to which tobacco is subjected to in the art. A "processed tobacco leaf" comprises no or substantially no viable cells.

The term "viable cells" refers to cells which are able to grow and/or are metabolically active. Thus, if a cell is said to not be viable, also referred to as "non-viable" then a cell does not display the characteristics of a viable cell.

The term "substantially no viable cells" means that less than about 5% of the total cells are viable. Preferably, less than about 3%, more preferably less than about 1%, even more preferably less than about 0.1% of the total cells are viable.

In one embodiment the processed tobacco leaf may be processed by one or more of: curing, fermenting and/or pasteurizing.

"Reconstituted" as used herein may also be referred to as recon, recycled or homogenized sheet tobacco and refers to tobacco material generated from remnants of tobacco leaf after processing. Reconstituted tobacco allows the production of a consistent, high quality blend and allows the adjustment of the ratio of individual components.

Reconstituted tobacco may be nano fibre recon (nanofibers can be extracted in solid or liquid form), paper making recon (which uses stems, scraps, and midribs, etc. as the raw material) or slurry type recon (which uses a mixture of fines and tobacco stems, ground to power, mixed with water and vegetable binding agent. The soluble residue is formed to sheets by extracting the water.)

As used herein, the term "tobacco industry product" is intended to include combustible smoking articles such as cigarettes, cigarillos, cigars, tobacco for pipes or for roll-your-own cigarettes, (whether based on tobacco, tobacco derivatives, expanded tobacco, reconstituted tobacco, tobacco substitutes or other smokable material), non-combustible aerosol provision systems such as heating products that release compounds from substrate materials without burning such as electronic cigarettes, tobacco heating products, and hybrid systems to generate aerosol from a combination of substrate materials, for example hybrid systems containing a liquid or gel or solid substrate, as well as aerosolizable substrate materials used within these aerosol provision systems; and aerosol-free delivery articles such as lozenges, gums, patches, articles comprising breathable powders and smokeless tobacco industry products such as snus and snuff, which aerosol-free delivery articles may or may not deliver nicotine.

The term "part thereof" as used herein in the context of a tobacco plant refers to a portion of the tobacco plant. Suitably, the "part thereof" may be a leaf, root or stem of a tobacco plant or the flowers. Suitably, the "part thereof" may be a leaf, root or stem of a tobacco plant. Preferably the "part thereof" is a leaf of a tobacco plant.

As used herein, the term "smoking article" can include smokeable products, such as rolling tobacco, cigarettes, cigars and cigarillos whether based on tobacco, tobacco derivatives, expanded tobacco, reconstituted tobacco or tobacco substitutes.

The term "smokeless tobacco industry product" as used herein refers to a tobacco industry product that is not intended to be smoked and/or subjected to combustion.

Smokeless tobacco industry products (including heat-not-burn materials) may contain tobacco in any form, including dried particles, shreds, granules, powders, or slurry, deposited on, mixed in, surrounded by, or combined with other ingredients in any format, such as flakes, films, tabs, foams, or beads.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

All combinations of method or process steps as used herein can be performed in any order, unless otherwise specified or clearly implied to the contrary by the context in which the referenced combination is made.

DETAILED DESCRIPTION

The details of one or more embodiments of the presently-disclosed subject matter are set forth in this document.

Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter relates to articles and methods for regulating conversion of nicotine to nornicotine and/or regulating levels of tobacco specific (TSNA) precursors. In some embodiments, the article includes one or more transcription factor (TF) inhibitors. In one embodiment, for example, the article includes one or more inhibitors of basic region/leucine zipper (bZIP) type transcription factors. In another embodiment, the bZIP type transcription factors are derived from tobacco. In a further embodiment, of the 133 bZIP type transcription factors identified in tobacco by the instant inventors, which are classified into ten sub-groups: A, B, C, D, E, F, G, H, and S, suitable bZIP type transcription factors include at least one of the 27 bZIPs in sub-group S, at least one of the 6 bZIPs in sub-group C, other bZIP 63 homologs, or a combination thereof. In certain embodiments, the S sub-group bZIP transcription factor includes, but is not limited to, NtbZIP1a (SEQ ID NOs: 1 and 2), NtbZIP1b (SEQ ID NOs: 3 and 4), or a combination thereof; and/or the C sub-group bZIP transcription factor includes, but is not limited to, NtbZIP2a (SEQ ID NO: 5), NtbZIP2b (SEQ ID NO: 6), or a combination thereof.

The one or more transcription factor inhibitors include, but are not limited to, antisense oligonucleotides, miRNA, siRNA, locked nucleic acid (LNA) nucleotides, or a combination thereof. In some embodiments, the inhibitors provide RNAi-mediated knock-down/silencing of the bZIP type transcription factors. As will be appreciated by those skilled in the art, the specific sequence/structure of the transcription factor inhibitors is based upon the sequence of the specific transcription factor. Accordingly, as will also be appreciated by those skilled in the art, the antisense oligonucleotides and/or LNAs may be formed by any suitable method using the bZIP type transcription factor sequences provided herein. For example, in one embodiment, the inhibitor includes an antisense oligonucleotide having 100% sequence homology with the complementary bZIP type transcription factor. In another embodiment, the transcription factor inhibitor includes an antisense oligonucleotide having 100% sequence homology with a bZIP type transcription factor complementary to NtbZIP1a, NtbZIP1b, NtbZIP2a, and/or NtbZIP2b. In such embodiments, the transcription factor inhibitor(s) provide RNAi-mediated knock-down/silencing of NtbZIP1a, NtbZIP1b, NtbZIP2a, and/or NtbZIP2b expression in tobacco.

Also provided herein, in some embodiments, is a method of regulating the conversion of nicotine to nornicotine in a tobacco plant or other nicotine containing organism. In one embodiment, the method includes administering one or more of the bZIP inhibitors disclosed herein to a nicotine containing organism. Administration of these one or more bZIP inhibitors decreases or eliminates conversion of the nicotine to nornicotine. The one or more inhibitors may be administered for a single type of bZIP transcription factor, or for a combination of bZIP transcription factors. For example, in one embodiment, the method includes administering one or more inhibitors for S bZIP type transcription factors or C bZIP type transcription factors. In another embodiment, the method includes administering one or more inhibitors for S bZIP type transcription factors and one or more transcription factors for C bZIP type transcription factors. In a further embodiment, the method includes administering one or more inhibitors of NtbZIP1a, NtbZIP1b, NtbZIP2a, and/or NtbZIP2b to the organism. In certain embodiments, inhibiting both S bZIP type transcription factors and C bZIP type transcription factors has a synergistic effect on the reduction or elimination of nicotine conversion to nornicotine.

The methods disclosed herein include administering a single type of inhibitor or any suitable combination of inhibitors, which may be the same or different for each bZIP transcription factor being inhibited. For example, in one embodiment, the method includes administering antisense oligonucleotides of NtbZIP1a, NtbZIP1b, NtbZIP2a, and/or NtbZIP2b. In another embodiment, the method includes administering antisense oligonucleotides of one bZIP transcription factor, such as NtbZIP1a, and LNA nucleotides of another bZIP transcription factor, such as NtbZIP1b. As will be appreciated by those skilled in the art, although discussed above with regard to certain combinations of bZIP transcription factors and transcription factor inhibitors, the disclosure is not so limited and may include any other suitable combination of TFs and TF inhibitors.

Additionally or alternatively, the method may include bZIP type transcription factor knockout and/or mutation of a bZIP type transcription factor binding site on the promoter of the nicotine N-demethylase (NND). For example, in one embodiment, the method includes editing the plant genome to knock-out NtbZIP1a, NtbZIP1b, NtbZIP2a, and/or NtbZIP2b. The genome editing may be performed through any suitable process, such as, but not limited to, CRISPR/Cas9-mediated genome editing. In another embodiment, the method includes mutating the bZIP binding element in the E4 promoter, called A/G box (TACGTC), to TGCGTC by site-directed mutagenesis. Although discussed above with regard to a specific mutation in the E4 promoter, as will be appreciated by those skilled in the art, the disclosure is not so limited and includes any other mutation in the E4, E5, and/or E10 promoter to reduce or eliminate activation of the respective NND by the bZIP type transcription factor.

The administration of the TF inhibitors, the TF knockout, and/or the binding site mutation disclosed herein reduces or eliminates activation of the NND by the bZIP type transcription factor, which decreases or eliminates conversion of nicotine to nornicotine. As opposed to existing articles that include E4, E5, and E10 mutants, the articles disclosed herein control the expression of E4, E5, and E10 to reduce or eliminate the conversion of nicotine to nornicotine. By reducing or eliminating the conversion of nicotine to nornicotine the articles and methods disclosed herein decrease the harmful effects of products which typically contain the carcinogenic nornicotine, such as, but not limited to, tobacco products.

The presently disclosed subject matter includes methods of decreasing conversion of nicotine to nornicotine and/or methods of reducing levels of at least one tobacco specific (TSNA) precursor, which involve reducing the activity and/or expression of at least one basic region/leucine zipper (bZIP) type transcription factor in a tobacco plant, a part of a tobacco plant, a tobacco plant seed, or another nicotine containing organism.

The presently disclosed subject matter further includes use of a reduction in the activity and/or expression of at least one basic region/leucine zipper (bZIP) type transcription factor in a tobacco plant, a part of a tobacco plant, a tobacco plant cell, a tobacco plant seed, or another nicotine containing organism for decreasing conversion of nicotine to nornicotine and/or for reducing levels of at least one tobacco specific (TSNA) precursor in the tobacco plant, part of a tobacco plant, tobacco plant seed, or nicotine containing organism.

In embodiments of the methods and uses described herein, at least one bZIP transcription factor can be selected from the group consisting of group C bZIP transcription factor, group S bZIP transcription factor, and combinations thereof. In some embodiments, the at least one bZIP transcription factor is selected from the group consisting of NtbZIP1a, NtbZIP1b, NtbZIP2a, NtbZIP2b, and combinations thereof.

In some embodiments, the at least one bZIP transcription factor comprises an amino acid molecule having at least 90%, 95%, 97%, 98%, 99%, or 100% identity to an amino acid selected from the group consisting of the amino acid encoded by SEQ ID NO: 1; the amino acid of SEQ ID NO: 2; the amino acid encoded by SEQ ID NO: 3; the amino acid of SEQ ID NO: 4; the amino acid of SEQ ID NO: 5; and the amino acid of SEQ ID NO: 6.

In some embodiments, the at least one bZIP transcription factor comprises NtbZIP1a and NtbZIP1b. In some embodiments, the at least one bZIP transcription factor comprises NtbZIP2a and NtbZIP2b. In some embodiments, the at least one bZIP transcription factor comprises NtbZIP1a, NtbZIP1b, NtbZIP2a, and NtbZIP2b.

In some embodiments, the at least one bZIP transcription factor comprises an amino acid molecule having at least 90%, 95%, 97%, 98%, 99%, or 100% identity to an amino acid selected from the group consisting of the amino acid encoded by SEQ ID NO: 1 and the amino acid of SEQ ID NO: 2; and an amino acid molecule having at least 90%, 95%, 97%, 98%, 99%, or 100% identity to an amino acid selected from the group consisting of the amino acid encoded by SEQ ID NO: 3 and the amino acid of SEQ ID NO: 4

In some embodiments, the at least one bZIP transcription factor comprises an amino acid molecule having at least 90%, 95%, 97%, 98%, 99%, or 100% identity to the amino acid of SEQ ID NO: 5; and an amino acid molecule having at least 90%, 95%, 97%, 98%, 99%, or 100% identity to the amino acid of SEQ ID NO: 6.

In some embodiments, the at least one bZIP transcription factor comprises an amino acid molecule having at least 90%, 95%, 97%, 98%, 99%, or 100% identity to an amino acid selected from the group consisting of the amino acid encoded by SEQ ID NO: 1 and the amino acid of SEQ ID NO: 2; an amino acid molecule having at least 90%, 95%, 97%, 98%, 99%, or 100% identity to an amino acid selected from the group consisting of the amino acid encoded by SEQ ID NO: 3 and the amino acid of SEQ ID NO: 4; an amino acid molecule having at least 90%, 95%, 97%, 98%, 99%, or 100% identity to the amino acid of SEQ ID NO: 5; and an amino acid molecule having at least 90%, 95%, 97%, 98%, 99%, or 100% identity to the amino acid of SEQ ID NO: 6.

In embodiments of the methods and uses described herein, reducing the activity and/or expression of the at least one bZIP type transcription factor can involve mutating the bZIP type transcription factor, such as providing a mutation in a binding site of the bZIP type transcription factor; using a bZIP type transcription factor inhibitor; or using a gene silencing technique, such as RNAi.

In some embodiments, the bZIP transcription factor inhibitor is selected from the group consisting of antisense oligonucleotides, miRNA, siRNA, locked nucleic acid (LNA) nucleotides, and combination thereof.

In some embodiments, mutating the bZIP type transcription factor comprises mutating the binding site on a promoter of a nicotine N-demethylase (NND). In some embodiments, the NND is selected from the group consisting of CYP82E4v1, CYP82E5v2, and CYP82E10. In some embodiments, the NND is CYP82E4v1 and wherein the bZIP binding site on the promoter of CYP82E4v1 is an A/G box with a pre-mutated sequence of TACGTC. In some embodiments, the mutated binding site has the sequence TGCGTC. In some embodiments, the mutated binding site is formed by site-directed mutagenesis.

In some embodiments, mutating the bZIP type transcription factor comprises mutating a plant genome to knockout at least one basic region/leucine zipper (bZIP) type transcription factor.

The present invention further includes nucleic acid molecules and amino acid molecules as described herein. In some embodiments, the isolated nucleic acid molecule can include a nucleic acid sequence having at least 90%, 95%, 97%, 98%, 99%, or 100% identity to the sequence of SEQ ID NO: 1 or SEQ ID NO: 3; a nucleic acid sequence encoding a sequence having at least 90%, 95%, 97%, 98%, 99%, or 100% identity to the sequence of SEQ ID NOs: 2, 4, 5, or 6; or combinations thereof.

In some embodiments the amino acid molecule can include an amino acid sequence having at least 90%, 95%, 97%, 98%, 99%, or 100% identity to an amino acid encoded by the sequence of SEQ ID NO: 1 or SEQ ID NO: 3; a sequence having at least 90%, 95%, 97%, 98%, 99%, or 100% identity to the sequence of SEQ ID NOs: 2, 4, 5, or 6; or combinations thereof.

In some embodiments, the molecule comprises or encodes a bZIP type transcription factor having at least one mutation. In some embodiments, the mutation is in the binding site on a promoter of a nicotine N-demethylase (NND). In some embodiments, the NND is selected from the group consisting of CYP82E4v1, CYP82E5v2, and CYP82E10. In some embodiments, the NND is CYP82E4v1 and wherein the bZIP binding site on the promoter of CYP82E4v1 is an A/G box with a pre-mutated sequence of TACGTC. In some embodiments, the mutated binding site has the sequence TGCGTC.

The presently-disclosed subject matter further includes a construct or vector comprising a nucleic acid molecule as disclosed herein.

The presently-disclosed subject matter further includes a tobacco plant cell, which can include an exogenous gene comprising a nucleic acid molecule as disclosed herein, can include a construct or vector as disclosed herein, can be obtained or is obtainable by as disclosed herein, and/or can be obtained by a mutation to reduce the activity or expression of at least one bZIP type transcription factor or to knockout at least one bZIP type transcription factor.

The presently-disclosed subject matter further includes the use of a tobacco cell as disclosed herein for the production of a tobacco industry product.

The presently-disclosed subject matter further includes a tobacco cell, cell culture, or plant that includes a plant cell as disclosed herein, which has been modified to achieve a decrease in conversion of nicotine to nornicotine and/or reduction in levels of at least one tobacco specific (TSNA) precursor of said culture or plant compared with that of an unmodified culture or plant; or which includes a construct or vector as disclosed herein.

Suitably a tobacco plant according to the present invention may have a e.g. reduced content of a tobacco specific nitrosamine (TSNA) precursor when compared to an unmodified tobacco plant. Suitably, the tobacco plant cell may be a mutant, non-naturally occurring or transgenic plant. The plant may comprise one or more mutations which reduce the activity and/or expression of at least one basic region/leucine zipper (bZIP) type transcription factor.

In one embodiment the tobacco plant in accordance with the present invention comprises a tobacco cell of the invention.

In another embodiment the plant propagation material may be obtainable (e.g. obtained) from a tobacco plant of the invention.

In one embodiment there is provided the use of a tobacco plant as described herein to breed a tobacco plant.

The present invention also provides in another embodiment the use of a tobacco plant of the foregoing embodiments for the production of a tobacco industry product.

In another embodiment there is provided the use of a tobacco plant of the invention to grow a crop.

In one embodiment there is provided the use of a cell as provided for in the foregoing embodiments for production of a tobacco industry product.

In one embodiment the present invention provides a cell (e.g. a tobacco plant cell) which has reduced activity and/or expression of at least one basic region/leucine zipper (bZIP) type transcription factor. Suitably, the cell may be a mutant, non-naturally occurring or transgenic cell. The cell may comprise one or more mutations which reduce the activity and/or expression of at least one basic region/leucine zipper (bZIP) type transcription factor.

In one embodiment the present invention provides a cell culture (e.g. in in vitro culture). Suitably the cell culture may comprise a plurality of cells according to the present invention.

The tobacco cell culture may be a cell suspension culture. These cells cultured in vitro may be incorporated into a tobacco industry product, e.g. as a substitute for conventional tobacco particles, shreds, fine cut or long cut tobacco lamina, as an additive ingredient or as both a substitute and an additive. Suitably, the cell culture may produce nicotine.

In one embodiment there is provided the use of a cell culture, e.g. a harvested and/or processed cell culture according to the present invention for the production of a tobacco industry product.

The cells harvested from an in vitro culture may be dried, e.g. freeze-dried, for example to produce a powder.

In one embodiment, the cell culture is a tobacco cell culture.

The skilled person will be aware of known methods for establishing in vitro cultures of tobacco cells. By way of example only the following method may be used: collecting seeds form a tobacco plant of interest and sterilizing their exterior to eliminate unwanted organisms, planting said seeds to grown a tobacco plant of interest, removing tissue from the tobacco plant (for example, from the tobacco stem) for use as an explant, establishing a callus culture form the tobacco explant, establishing a cell suspension culture from the callus culture, and harvesting culture material (e.g. including tobacco cells) to produce a tobacco cell culture.

The tobacco cells can be harvested by various methods, including filtration, e.g. vacuum filtration. The sample may be washed in the filter by adding water and the remaining liquid removed with the filtration, e.g. vacuum filtration.

The harvested tobacco cell culture may be further processed, e.g. dried, such as air-dried and/or freeze-dried. The harvested tobacco cell culture or dried harvested tobacco cell culture may be incorporated into tobacco industry products according to the present invention.

The presently-disclosed subject matter further includes a plant propagation material or a plant extract obtainable from a plant according to claim 34 or of a portion of said plant. In some embodiments, the plant propagation material is a plant seed.

The presently-disclosed subject matter further includes the use of a tobacco plant as disclosed herein to breed a tobacco plant.

The present invention also provides for products obtainable or obtained from tobacco according to the present invention.

In one embodiment there is provided the use of a tobacco plant of the invention to produce a tobacco leaf.

Suitably the tobacco leaf may be subjected to downstream applications such as processing.

Thus in one embodiment the use of the foregoing embodiment may provide a processed tobacco leaf. Suitably the tobacco leaf may be subjected to curing, fermenting, pasteurizing or combinations thereof. In another embodiment the tobacco leaf may be cut. In some embodiments the tobacco leaf may be cut before or after being subjected to curing, fermenting, pasteurizing or combinations thereof.

The presently-disclosed subject matter includes the use of a tobacco plant as disclosed herein for production of a tobacco industry product. The presently-disclosed subject matter further includes the use of a tobacco plant as disclosed herein to grow a crop. The presently-disclosed subject matter further includes the use of a tobacco plant as disclosed herein to produce a processed tobacco leaf. In some embodiments, the processed tobacco leaf is a cured tobacco leaf.

In one embodiment the present invention provides a harvested leaf of a tobacco plant of the invention. In a further embodiment the harvested leaf may be obtainable (e.g. obtained) from a tobacco plant propagated from a propagation material of the present invention. In another embodiment there is provided a harvest leaf obtainable from a method or use of the present invention. Suitably the harvested leaf may be a cut harvested leaf. In some embodiments the harvested leaf may comprise viable tobacco cells. In other embodiments the harvested leaf may be subjected to further processing.

There is also provided a processed tobacco leaf. The processed tobacco leaf may be obtainable from a tobacco plant of the invention. Suitably the processed tobacco leaf may be obtainable from a tobacco plant obtained in accordance with any of the methods and/or uses of the present invention. In another embodiment the processed tobacco leaf may be obtainable from a tobacco plant propagated form a tobacco plant propagation material according to the present invention. The processed tobacco leaf of the present invention may be obtainable by processing a harvested leaf of the invention.

Suitably the processed tobacco leaf may be processed by curing. Tobacco leaf may be cured by any method known in the art. In one embodiment tobacco leaf may be cured by one or more of the curing methods selected from the group consisting of: air curing, fire curing, flue curing and sun curing.

Suitably the tobacco leaf may be air cured. Typically air curing is achieved by hanging tobacco leaf in well-ventilated barns and allowing to dry. This is usually carried out over a period of four to eight weeks. Air curing is especially suitable for burley tobacco.

Suitably the tobacco leaf may be fire cured. Fire curing is typically achieved by hanging tobacco leaf in large barns where fires of hardwoods are kept on continuous or intermittent low smolder and usually takes between three days and ten weeks, depending on the process and the tobacco.

In another embodiment the tobacco leaf may be flue cured. Flue curing may comprise stringing tobacco leaves onto tobacco sticks and hanging them from tier-poles in curing barns. The barns usually have a flue which runs from externally fed fire boxes. Typically this results in tobacco that has been heat-cured without being exposed to smoke. Usually the temperature will be raised slowly over the course of the curing with the whole process taking approximately 1 week.

Suitably the tobacco leaf may be sun cured. This method typically involves exposure of uncovered tobacco to the sun.

Suitably the processed tobacco leaf may be processed by fermenting. Fermentation can be carried out in any manner known in the art. Typically during fermentation, the tobacco leaves are piled into stacks (a bulk) of cured tobacco covered in e.g. burlap to retain moisture. The combination of the remaining water inside the leaf and the weight of the tobacco generates a natural heat which ripens the tobacco. The temperature in the center of the bulk is monitored daily. In some methods every week, the entire bulk is opened. The leaves are then removed to be shaken and moistened and the bulk is rotated so that the inside leaves go outside and the bottom leaves are placed on the top of the bulk. This ensures even fermentation throughout the bulk. The additional moisture on the leaves, plus the actual rotation of the leaves themselves, generates heat, releasing the tobacco's natural ammonia and reducing nicotine, while also deepening the color and improving the tobacco's aroma. Typically the fermentation process continues for up to 6 months, depending on the variety of tobacco, stalk position on the leaf, thickness and intended use of leaf.

Suitably the processed tobacco leaf may be processed by pasteurizing. Pasteurizing may be particularly preferred when the tobacco leaf will be used to make a smokeless tobacco industry product, most preferably snus.

Tobacco leaf pasteurization may be carried out by any method known in the art. For example pasteurization may be carried out as detailed in J Foulds, L Ramstrom, M Burke, K Fagerstrom. Effect of smokeless tobacco (snus) on smoking and public health in Sweden. Tobacco Control (2003) 12: 349-359, the teaching of which is incorporated herein by reference.

During the production of snus pasteurization is typically carried out by a process in which the tobacco is heat treated with steam for 24-36 hours (reaching temperatures of approximately 100° C.). This results in an almost sterile product and without wishing to be bound by theory one of the consequences of this is believed to be a limitation of further TSNA formation.

In one embodiment the pasteurization may be steam pasteurization.

In some embodiments the processed tobacco leaf may be cut. The processed tobacco leaf may be cut before or after processing. Suitably, the processed tobacco leaf may be cut after processing. In one embodiment, the use of the foregoing embodiment may provide reconstituted tobacco.

Any method known in the art may be used for making reconstituted tobacco, for example see CORESTA Congress, Sapporo, 2012, Smoke Science/Product Technology Groups, SSPT 12 (incorporated herein by reference).

In some embodiments the tobacco plant, harvested leaf of a tobacco plant and/or processed tobacco leaf may be used to extract nicotine. The extraction of nicotine can be achieved using any method known in the art. For example a method for extracting nicotine from tobacco is taught in U.S. Pat. No. 2,162,738 which is incorporated herein by reference.

In one aspect, the present invention provides cured tobacco material made from a tobacco plant or part thereof according to the invention.

In another aspect, the present invention provides a tobacco blend comprising tobacco material made from a tobacco plant or part thereof according to the present invention, or from a tobacco cell culture according to the present invention. In one aspect, the present invention provides a tobacco blend comprising cured tobacco material according to the present invention.

Suitably, the tobacco blend according to the present invention may comprise approximately 10%, 20%, 30%, 40%, 50%, 60%, 70%, 80% or 90% tobacco from a tobacco plant or part thereof according to the present invention, or from a tobacco cell culture according to the present invention. Suitably, the tobacco blend may comprise approximately 10% tobacco from a tobacco plant or part thereof according to the present invention, or from a tobacco cell culture according to the present invention. Suitably, the tobacco blend may comprise approximately 20% tobacco from a tobacco plant or part thereof according to the present invention, or from a tobacco cell culture according to the present invention. Suitably, the tobacco blend may comprise approximately 30% tobacco from a tobacco plant or part thereof according to the present invention, or from a tobacco cell culture according to the present invention. Suitably, the tobacco blend may comprise approximately 40% tobacco from a tobacco plant or part thereof according to the present invention, or from a tobacco cell culture according to the present invention. Suitably, the tobacco blend may comprise approximately 50% tobacco from a tobacco plant or part thereof according to the present invention, or from a tobacco cell culture according to the present invention. Suitably, the tobacco blend may comprise approximately 60% tobacco from a tobacco plant or part thereof according to the present invention, or from a tobacco cell culture according to the present invention. Suitably, the tobacco blend may comprise approximately 70% tobacco from a tobacco plant or part thereof according to the present invention, or from a tobacco cell culture according to the present invention. Suitably, the tobacco blend may comprise approximately 80% tobacco from a tobacco plant or part thereof according to the present invention, or from a tobacco cell culture according to the present invention. Suitably, the tobacco blend may comprise approximately 90% tobacco from a tobacco plant or part thereof according to the present invention, or from a tobacco cell culture according to the present invention.

In one aspect, a tobacco blend product of the present invention comprises at least about 5, 10, 20, 30, 40, 50, 60, 70, 80, 90, or 95 percent by dry weight of tobacco cured from a tobacco plant or part thereof according to the present invention, or a tobacco cell culture according to the present invention.

Suitably, the cured tobacco material may be air cured. Suitably, the cured tobacco material may be flue cured. Suitably, the cured tobacco material may be sun cured. Suitably, the cured tobacco material may be fire cured.

A tobacco industry product or smoking article according to the present invention may comprise the tobacco material (e.g. cured tobacco material or reconstituted tobacco material) according to the present invention.

In another aspect the present invention provides a tobacco industry product. In one embodiment the tobacco industry product according to the present invention may be a blended tobacco industry product. Suitably, the tobacco blend may comprise cured tobacco material according to the present invention. In one embodiment the tobacco industry product may be prepared from a tobacco plant of the invention or a part thereof. Suitably the tobacco plant or part thereof may be propagated from a tobacco plant propagation material according to the present invention.

In one embodiment the tobacco industry product may be prepared from (e.g. may comprise) a tobacco plant of the invention or a part thereof.

Suitably the tobacco plant or part thereof may be propagated from a tobacco plant propagation material according to the present invention.

In another embodiment the tobacco industry product may be prepared from a harvested leaf of the invention.

In a further embodiment the tobacco industry product may be prepared from a processed tobacco leaf of the invention.

Suitably the tobacco industry product may be prepared from a tobacco leaf processed by one or more of: curing, fermenting and/or pasteurizing.

Suitably the tobacco industry product may comprise a cut tobacco leaf, optionally processed as per the foregoing embodiment.

In another embodiment, the tobacco industry product may be prepared from a tobacco cell culture according to the present invention.

In another embodiment, the tobacco industry product may be prepared from (e.g. may comprise) a cured tobacco material according to the present invention.

In another embodiment, the tobacco industry product may be prepared from (e.g. may comprise) a tobacco blend according to the present invention.

In one embodiment the tobacco industry product may be a smoking article.

In another embodiment the tobacco industry product may be a smokeless tobacco industry product.

In one embodiment a smokeless tobacco industry product may include snus, snuff, chewing tobacco or the like.

In one embodiment, the tobacco industry product is a combustible smoking article, selected from the group consisting of a cigarette, a cigarillo and a cigar.

In one embodiment, the tobacco industry product comprises one or more components of a combustible smoking article, such as a filter, a filter rod, a filter rod segments, tobacco, a tobacco rod, a tobacco rod segment, a spill, an additive release component such as a capsule, a thread, beads, a paper such as a plug wrap, a tipping paper or a cigarette paper.

In one embodiment, the tobacco industry product is a non-combustible aerosol provision system.

In one embodiment, the tobacco industry product comprises one or more components of a non-combustible aerosol provision system, such as a heater and an aerosolizable substrate.

In one embodiment, the aerosol provision system is an electronic cigarette also known as a vaping device.

In one embodiment the electronic cigarette comprises a heater, a power supply capable of supplying power to the heater, an aerosolizable substrate such as a liquid or gel, a housing and optionally a mouthpiece.

In one embodiment the aerosolizable substrate is contained in a substrate container. In one embodiment the substrate container is combined with or comprises the heater.

In one embodiment, the tobacco industry product is a heating product which releases one or more compounds by heating, but not burning, a substrate material. The substrate material is an aerosolizable material which may be for example tobacco or other non-tobacco products, which may or may not contain nicotine. In one embodiment, the heating product is a tobacco heating product.

In one embodiment, the heating product is an electronic device.

In one embodiment, the tobacco heating product comprises a heater, a power supply capable of supplying power to the heater, an aerosolizable substrate such as a solid or gel material.

In one embodiment the heating product is a non-electronic article.

In one embodiment the heating product comprises an aerosolizable substrate such as a solid or gel material and a heat source which is capable of supplying heat energy to the aerosolizable substrate without any electronic means, such as by burning a combustion material, such as charcoal.

In one embodiment the heating product also comprises a filter capable of filtering the aerosol generated by heating the aerosolizable substrate.

In some embodiments the aerosolizable substrate material may comprise a vapor or aerosol generating agent or a humectant, such as glycerol, propylene glycol, triacetin or diethylene glycol.

In one embodiment, the tobacco industry product is a hybrid system to generate aerosol by heating, but not burning, a combination of substrate materials. The substrate materials may comprise for example solid, liquid or gel which may or may not contain nicotine. In one embodiment, the hybrid system comprises a liquid or gel substrate and a solid substrate. The solid substrate may be for example tobacco or other non-tobacco products, which may or may not contain nicotine. In one embodiment, the hybrid system comprises a liquid or gel substrate and tobacco.

In a further embodiment the tobacco industry product may be a tobacco heating device or hybrid device or e-cigarette or the like.

Typically in tobacco heating devices or hybrid devices, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user.

Aerosol-generating articles and devices for consuming or smoking tobacco heating devices are known in the art. They can include, for example, electrically heated aerosol-generating devices in which an aerosol is generated by the transfer of heat from one or more electrical heating elements of the aerosol-generating device to the aerosol-forming substrate of a tobacco heating device.

Suitably the tobacco heating device may be an aerosol-generating device. Preferably the tobacco heating device may be a heat-not-burn device. Heat-not-burn devices are known in the art and release compounds by heating, but not burning, tobacco. An example of a suitable, heat-not-burn device may be one taught in WO2013/034459 or GB2515502 which are incorporated herein by reference.

In one embodiment the aerosol-forming substrate of a tobacco heating device may be a tobacco industry product in accordance with the present invention. In one embodiment the tobacco heating device may be a hybrid device.

In a further embodiment there is provided the use of a nucleotide sequence of at least one gene encoding at least one bZIP type transcription factor having at least one mutation, wherein the sequence of the bZIP type transcription factor includes: a sequence encoded by a nucleic acid sequence comprising a nucleic acid sequence having at least one mutation relative to the sequence of SEQ ID NO: 1 or SEQ ID NO: 3; a sequence having at least one mutation relative to the sequence of SEQ ID NOs: 2, 4, 5, or 6; or combinations thereof to select a plant having reduced content of tobacco specific nitrosamine (TSNA) or a precursor of a TSNA.

In one embodiment, there is provided a mutant of a plant carrying at least one heritable mutation in at least one bZIP transcription factor encoded by a nucleic acid sequence comprising a nucleic acid sequence having at least one mutation relative to the sequence of SEQ ID NO: 1 or SEQ ID NO: 3; a sequence having at least one mutation relative to the sequence of SEQ ID NOs: 2, 4, 5, or 6; or combinations thereof; wherein said heritable mutations decrease the content of a tobacco specific nitrosamine (TSNA) or a precursor of a TSNA in the mutant tobacco plant relative to a comparable plant which does not carry said heritable mutations.

In another embodiment, there is provided progeny or seed of a mutant plant which carries the heritable mutation according to the present invention.

In a further embodiment, there is provided a harvested leaf, a processed leaf or cured tobacco material produced from a plant comprising at least one mutation in at least one bZIP transcription factor encoded by a nucleic acid sequence comprising a nucleic acid sequence having at least one mutation relative to the sequence of SEQ ID NO: 1 or SEQ ID NO: 3; a sequence having at least one mutation relative to the sequence of SEQ ID NOs: 2, 4, 5, or 6; or combinations thereof and wherein said plant has decreased content of a tobacco specific nitrosamine (TSNA) or a precursor of a TSNA relative to a comparable plant which does not carry said mutations in said bZIP transcription factors.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Example 1

Figure 2:
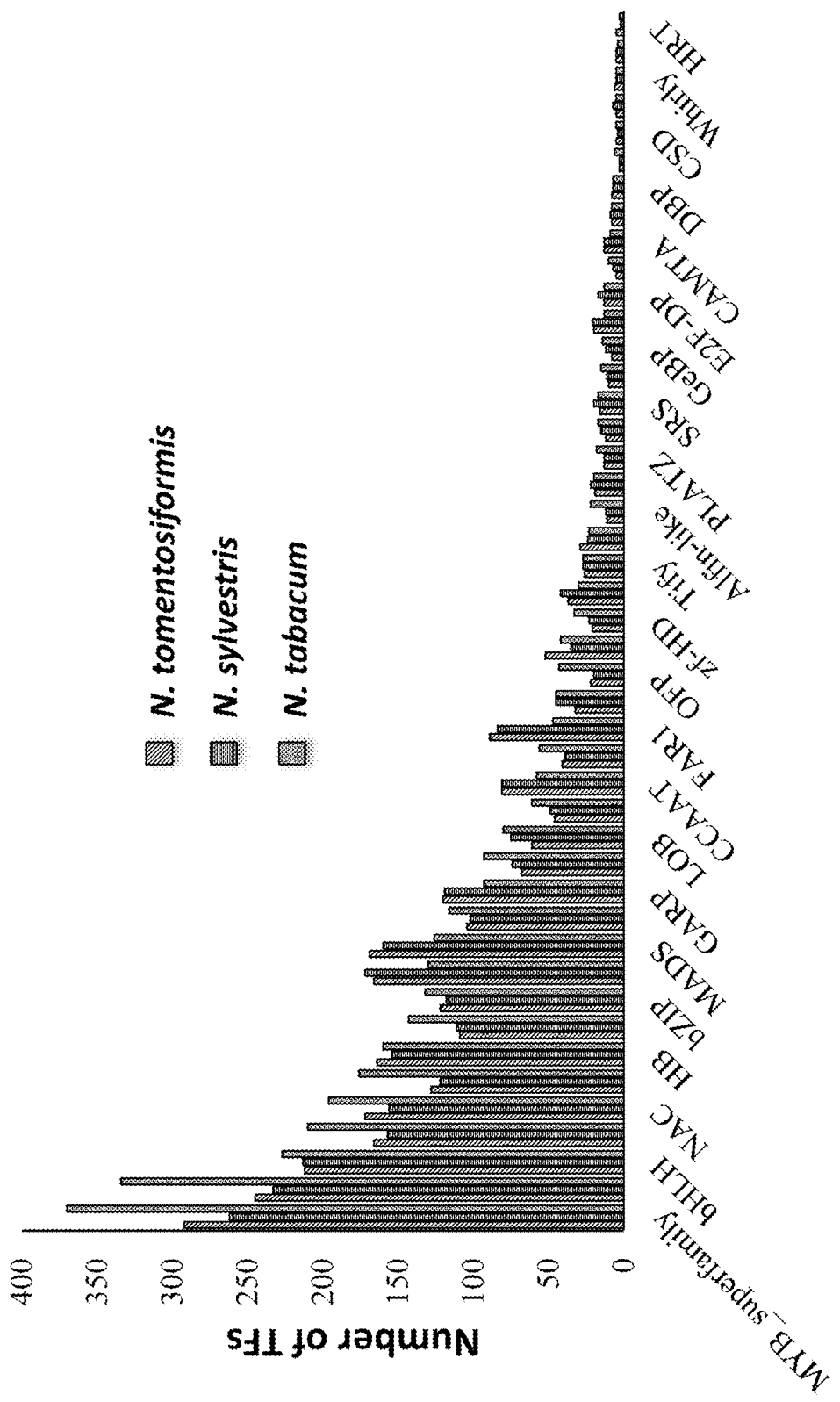
FIG. 2 shows a graph illustrating distribution of different TF families in tobacco and its progenitors.
Figure 3:
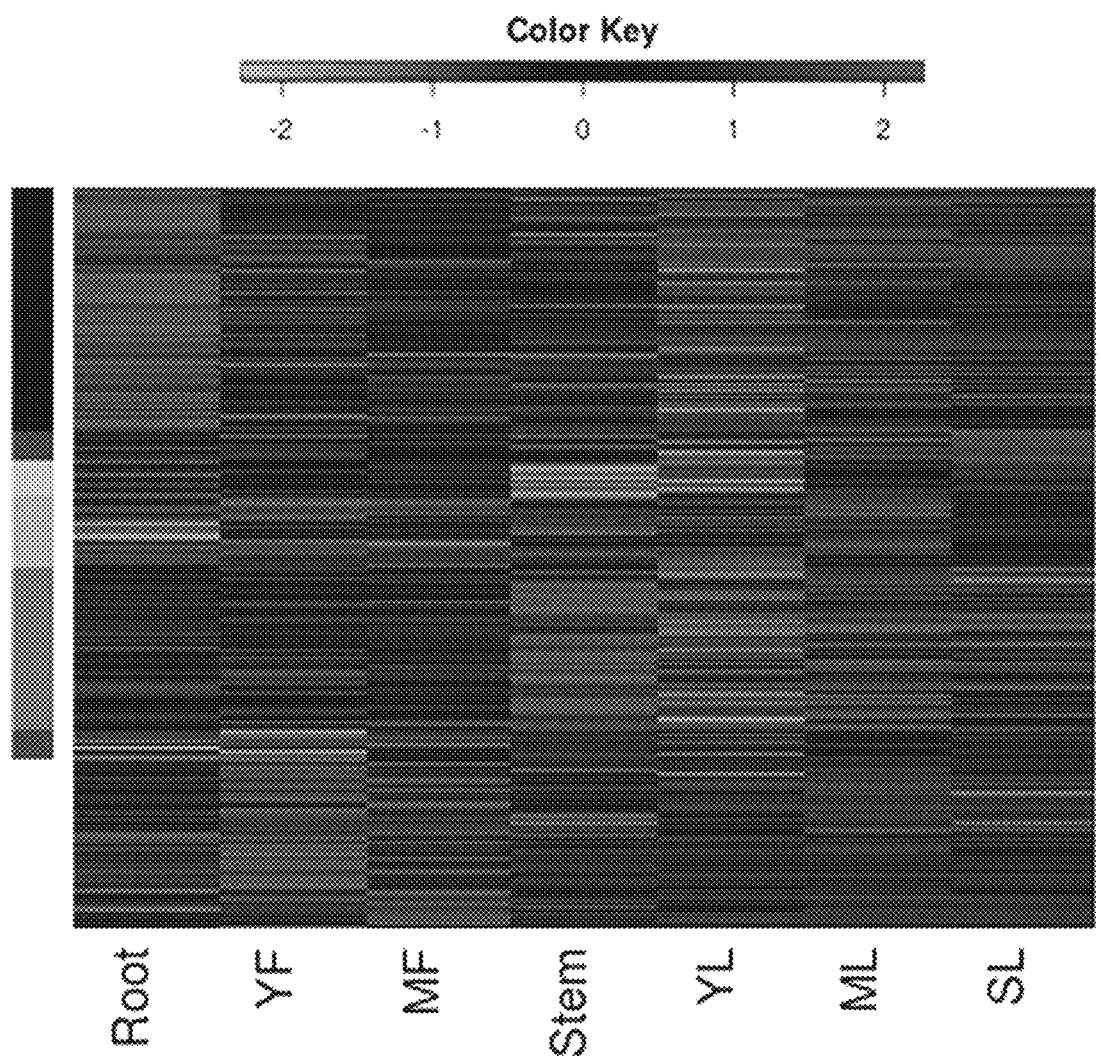
FIG. 3 shows a graph illustrating co-expression analysis of TF genes, and structural genes in nicotine biosynthetic pathway in different tissue. The TF and structural genes are grouped into 8 different modules (color-coded side bar) based on their expression. The black module contains majority of the structural gene nicotine biosynthetic pathway. YF, young flower; MF, mature flower; YL, young leaf; ML, mature leaf; SL, senesce leaf.

This Example describes the analysis of transcriptome data sets of different tobacco tissues, including leaf (young, mature, and senesce leaf), root, stem, flower (young and mature flower), and capsule to generate a co-expression network. First, a hierarchical cluster analysis was performed, which revealed that each individual tissue type exhibits a unique expression pattern (FIG. 1). Next, the genes encoding all major TF families in tobacco and its progenitors were identified. The tobacco genome contains more TF genes than its progenitors and the number of TFs belonging to MYB, AP2/ERFs, and bHLH families are significantly higher than other families (FIG. 2). In view thereof, the TFs and structural genes in the nicotine biosynthetic pathway were then grouped into 8 different modules (color-coded side bar) based on their expression pattern in different tissues (FIG. 3). The "black" module is particularly interesting as majority of the nicotine biosynthetic genes were found in this module along with a number of TF genes. Many of these TFs belong to MYB, bHLH, bZIP, and ERF families. As discussed in Examples 2-4 below, the role of these TFs in nicotine biosynthesis in tobacco is established through isolation and functional characterization thereof.

Example 2

This Example describes two bZIP type transcription factors from tobacco (FIG. 4), which regulate the conversion of nicotine to nornicotine, can be used for reduction of smoking related carcinogen, tobacco specific nitrosamines (TSNA).

bZIP TFs are characterized by a conserved leucine zipper motif that mediates dimer formation for DNA binding. In plants, bZIP TFs regulate processes including pathogen defense, light and stress signaling, seed maturation, and flower development. Many bZIP factors, especially those in tobacco, are not well characterized. By co-expression and clustering analyses, two bZIP TF genes that co-express with E4, E5, and E10 were identified herein. These tobacco bZIP TFs have been termed NtbZIP1a and NtbZIP1b.

Figure 4:
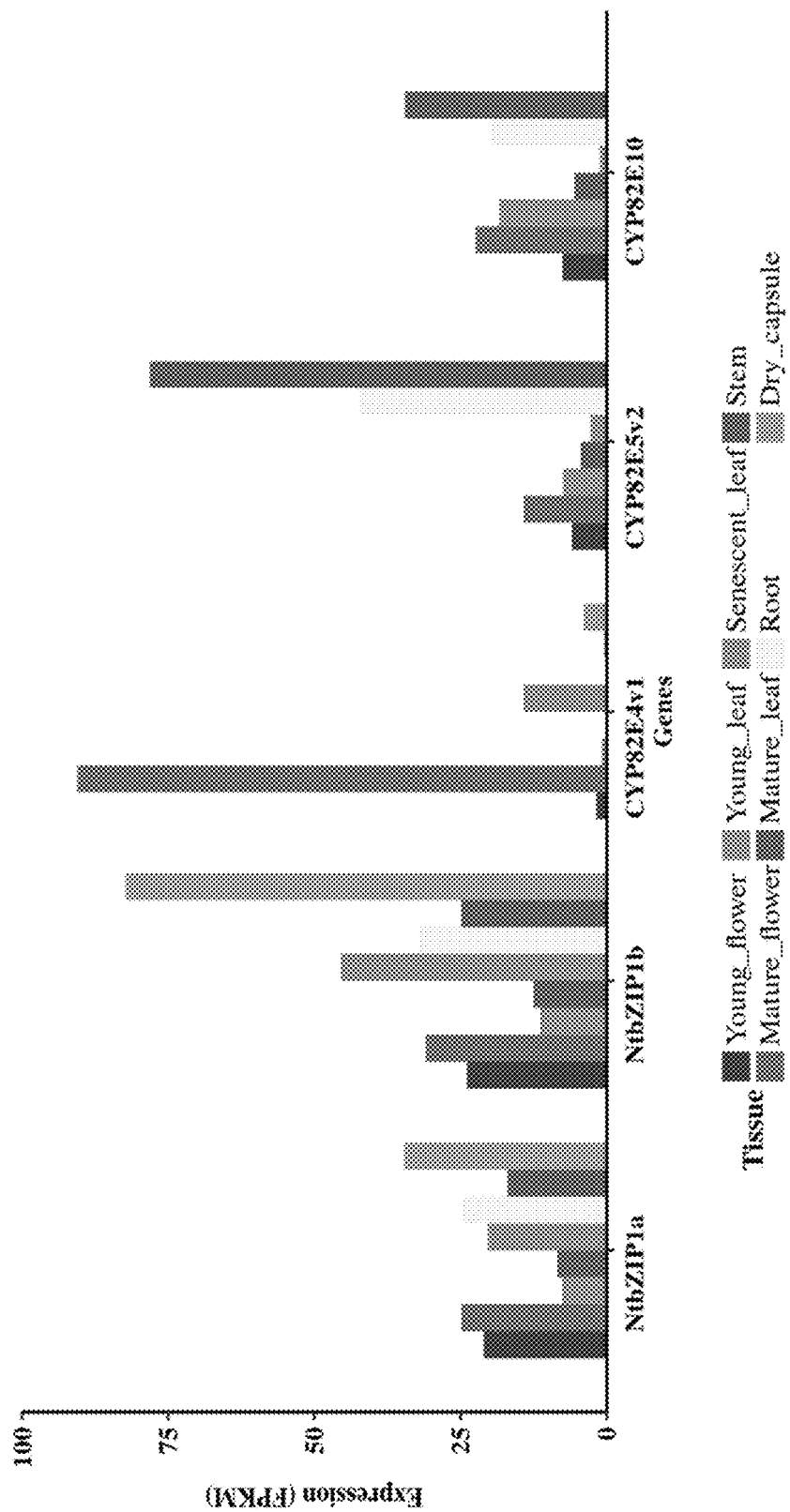
FIG. 4 shows a graph illustrating expression of NtbZIP1a/b and NNDs in different tobacco tissues.
Figure 5:
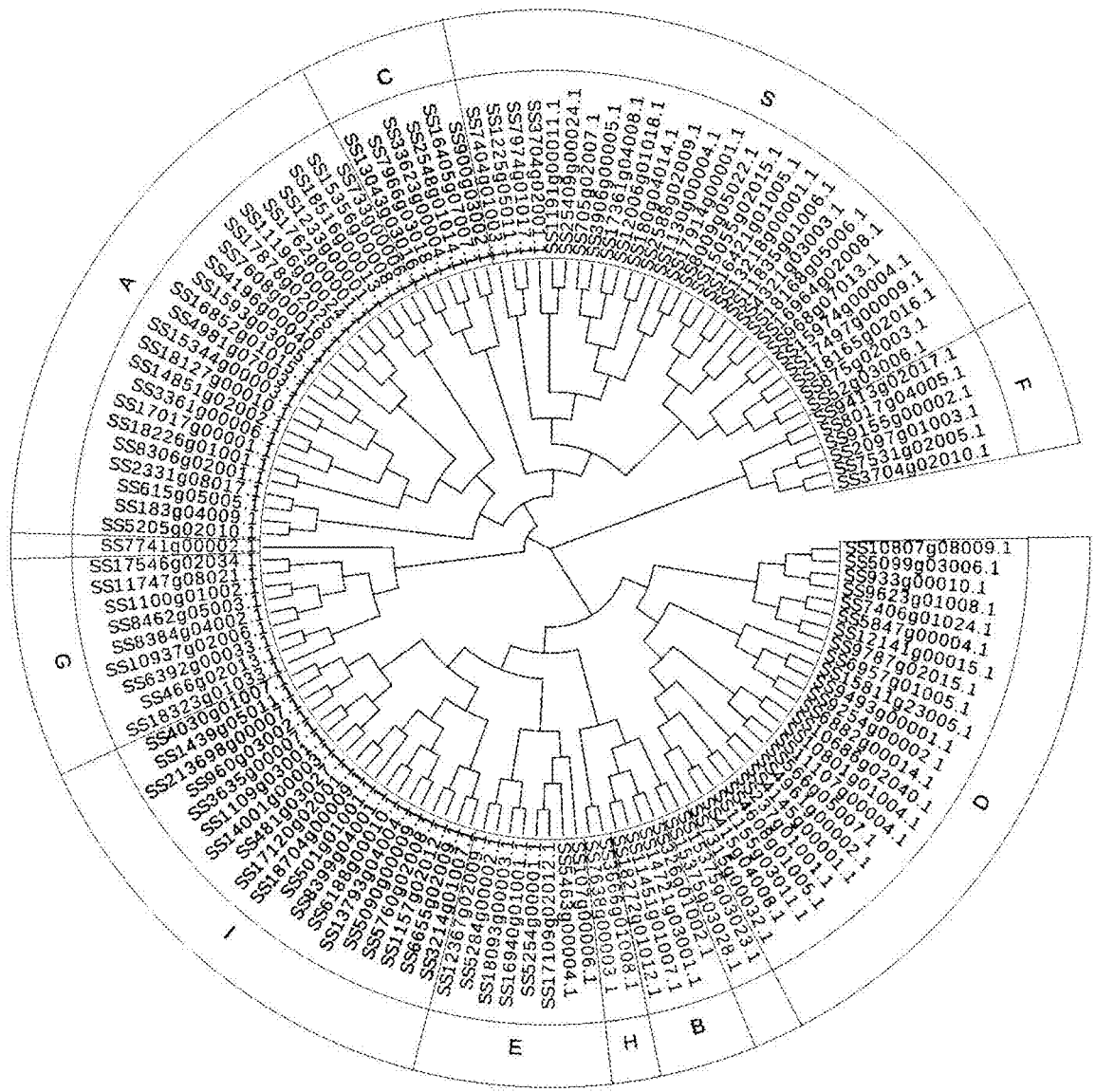
FIG. 5 shows an image illustrating the bZIP family in tobacco. NtbZIP1a and NtbZIP1b are indicated by *.
Figure 6:
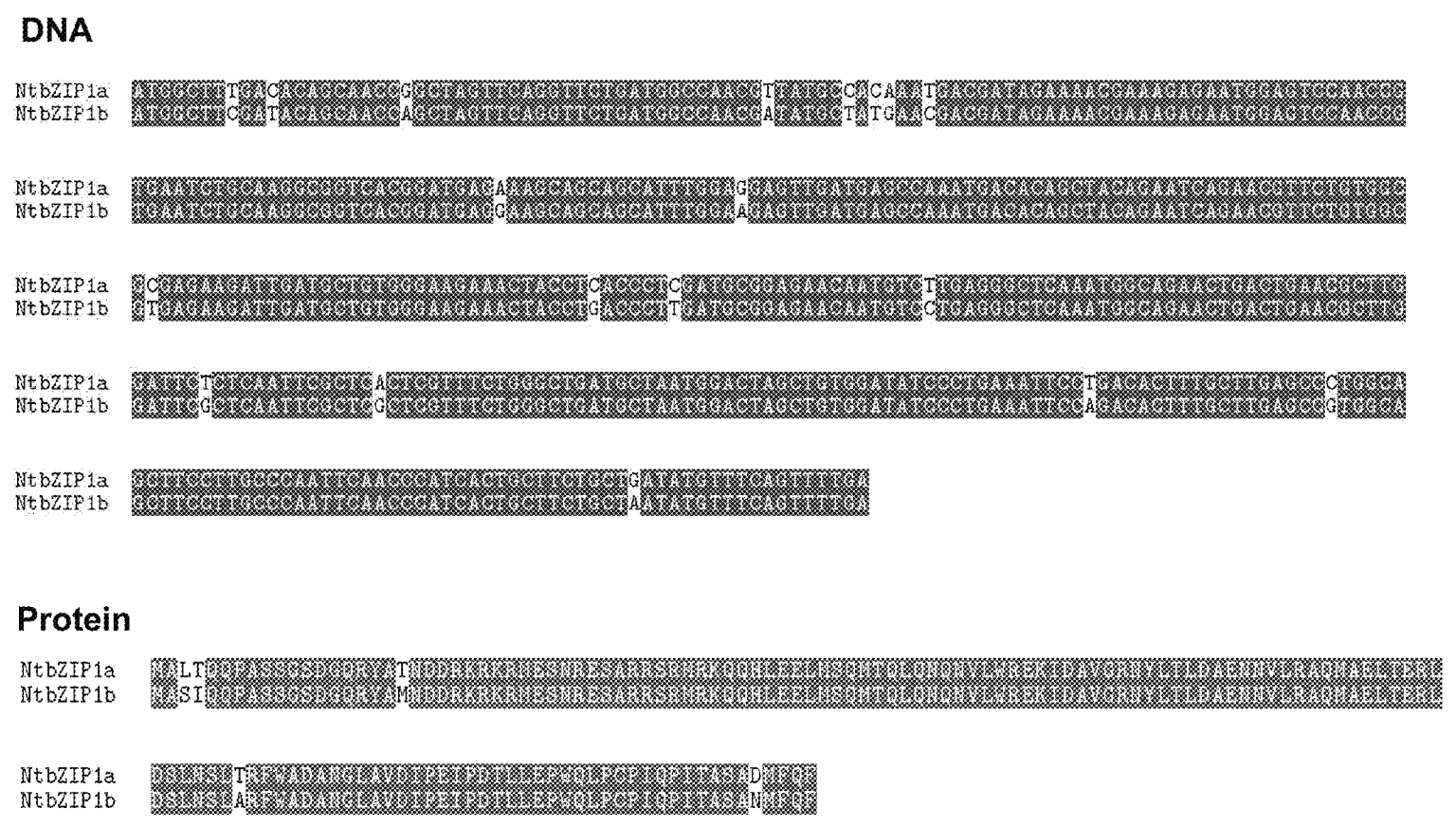

NtbZIP1 a/b exhibit similar expression patterns as compared to CYP82E4v1, the major NND enzyme involved in nicotine to nornicotine conversion, and are highly expressed in flowers and senescent leaves (FIG. 4). As illustrated in FIG. 5, 133 bZIPs were identified in tobacco and classified into ten sub-groups: A, B, C, D, E, F, G, H, I, and S, with NtbZIP1 a/b belonging to sub-group S. In maize, expression of group-S bZIPs are induced by wounding, cold, and drought stress. Referring to FIG. 6, it was also found that NtbZIP1a and b are more than 97% identical at nucleotide and amino acid level. Without wishing to be bound by theory, it is believed that the two homologous bZIPs are derived from two progenitors of tobacco, *N. sylvestris* and *N. tometosiformis*.

Figure 7:
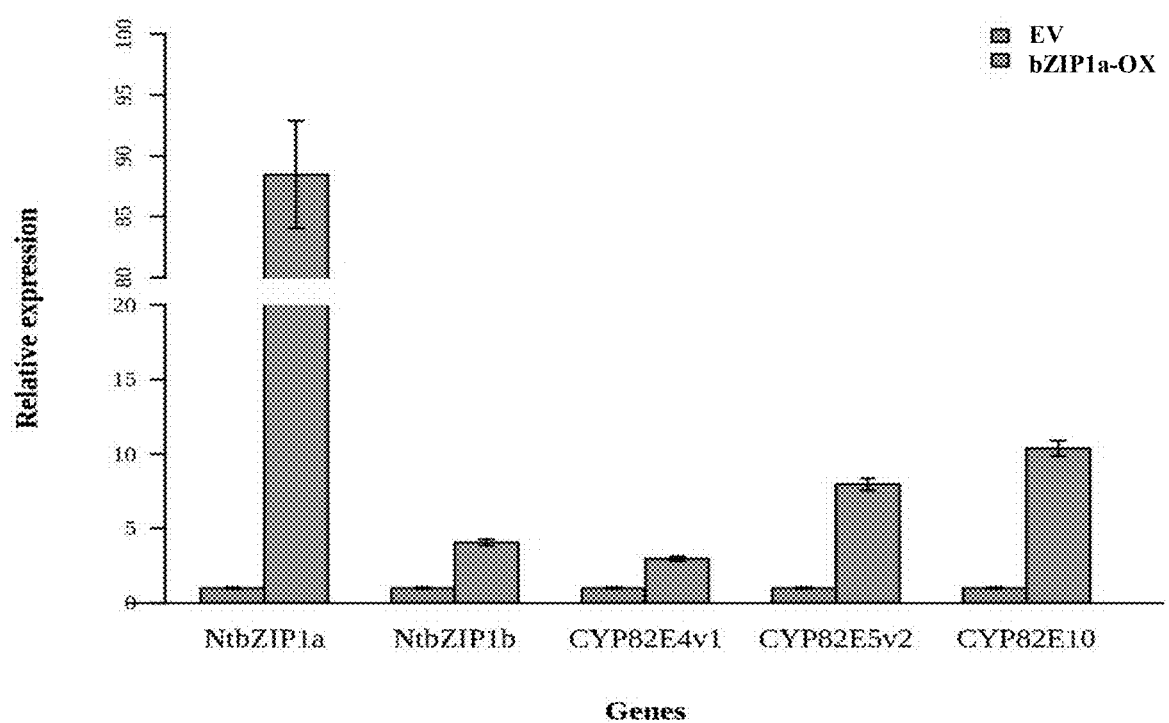
FIG. 7 shows a graph illustrating that transient overexpression of NtbZIP1a in tobacco leaves induces the expression of CYP82E4v1, CYP82E5v2, and CYP82E10.

After identifying the two bZIP TFs, whether overexpression of NtbZIP1a leads to upregulation of E4, 5, and 10 was tested. NtbZIP1a was cloned into pCAMBIA2300 (binary vector) under the control of the CaMV 35S promoter and rbcS terminator. The binary vectors (empty control and NtbZIP1a) were mobilized into *Agrobacterium*, and tobacco leaves were infiltrated using the transformed *Agrobacterium*. Total RNA isolated from *Agrobacterium*-infiltrated leaf discs were used for cDNA synthesis and real-time quantitative PCR (qRT-PCR) was used to detect the transcript levels of NtbZIP1a, NtbZIP1b, E4, 5, and 10. An ubiquitously expressed house-keeping gene, tubulin, was used as internal control in qRT-PCR. The results showed that, when NtbZIP1a was highly expressed transiently, the endogenous NtbZIP1b, E4, 5, and 10 were upregulated (approx. 3-10 fold), indicating that NtbZIP1a induces the expression of NtbZIP1b, E4, 5, and 10, hence a possible transcriptional activator for these genes (FIG. 7).

Figure 8:
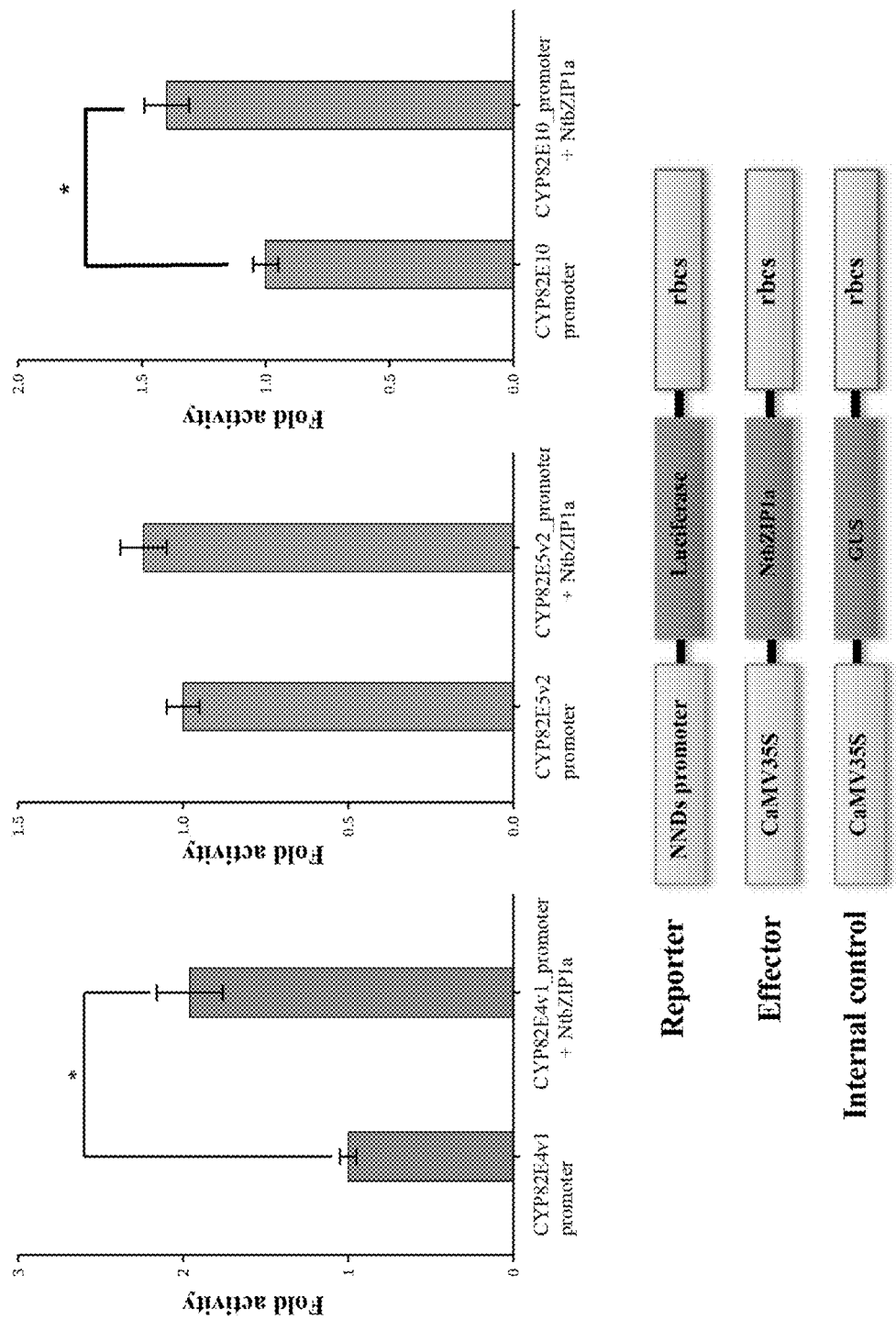
FIG. 8 shows a graph illustrating that NtbZIP1a significantly activates CYP82E4v1 and CYP82E10 promoters in tobacco cells.

Next, whether NtbZIP1a can bind to the promoters of its potential target genes was tested. The promoters (approximately 1.0 kb fragment of the 5' untranslated region of each coding gene) of E4, 5, and 10 were isolated, and the individual promoters were fused to a firefly luciferase reporter gene. The NtbZIP1a gene was cloned into the pBlueScript (pBS) vector under the control of the CaMV 35S promoter and rbcS terminator. The plasmids were electroporated into tobacco protoplasts. NtbZIP1a significantly induced the luciferase gene expression controlled by the E4 and E10 promoters, but not E5 promoter, suggesting that NtbZIP1a can directly activate E4 and E10 genes, likely by binding to their promoters (FIG. 8). NtbZIP1a did not appear to bind to the 1.0 kb promoter region of E5, used for the activation experiment. However, as mentioned above, overexpression of NtbZIP1a led to upregulation of E5, together with E4 and 10. The promoter activation experiment indicates two possible NtbZIP1a regulatory relationships with E5 gene: (1) NtbZIP1a binds to a site outside of the 1.0 kb promoter fragment, or (2) NtbZIP1a indirectly activates E5, through another unidentified activator in tobacco (e.g., NtbZIP1a activates another activator, which in turn activates E5).

Figure 9:
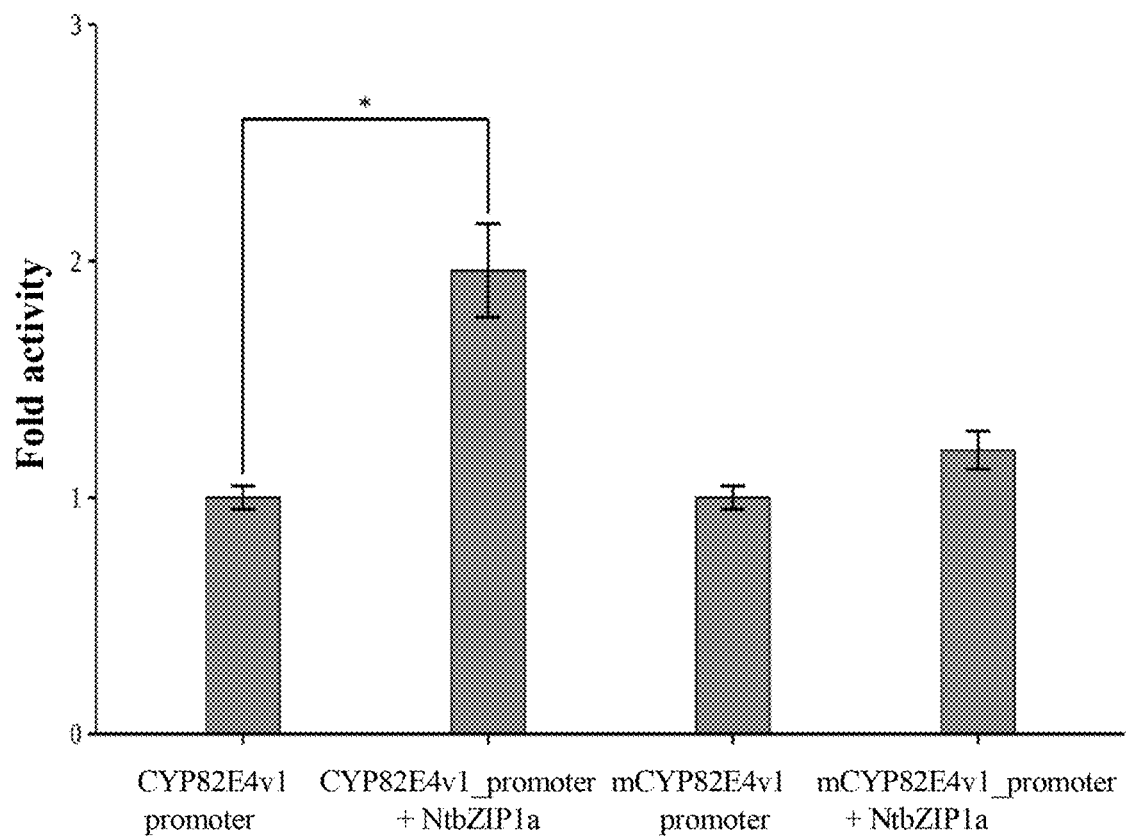
FIG. 9 shows a graph illustrating that NtbZIP1a activates CYP82E4v1 promoter in tobacco cells by binding to the A/G box.
Figure 9:
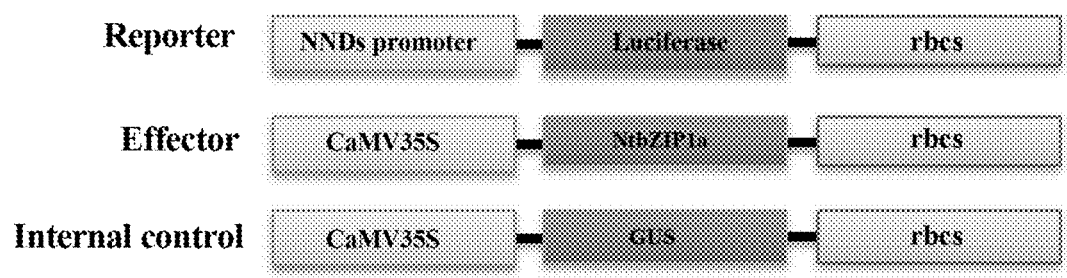

To support the possibility of NtbZIP1a directly binding to the E4 promoter to regulate transactivation the bZIP binding element in the E4 promoter, called A/G box (TACGTC), was mutated to TGCGTC by site-directed mutagenesis. The mutated promoter was fused to the luciferase reporter gene as described above. A transactivation experiment was then performed using the mutant reporter plasmid and the NtbZIP1a expression vector, as described above. The result showed that NtbZIP1a is unable to activate the luciferase gene expression under the control of the mutant promoter (FIG. 9). This experiment demonstrated that the E4 promoter is activated through an A/G-box binding factor, most likely NtbZIP1a.

Figure 10:
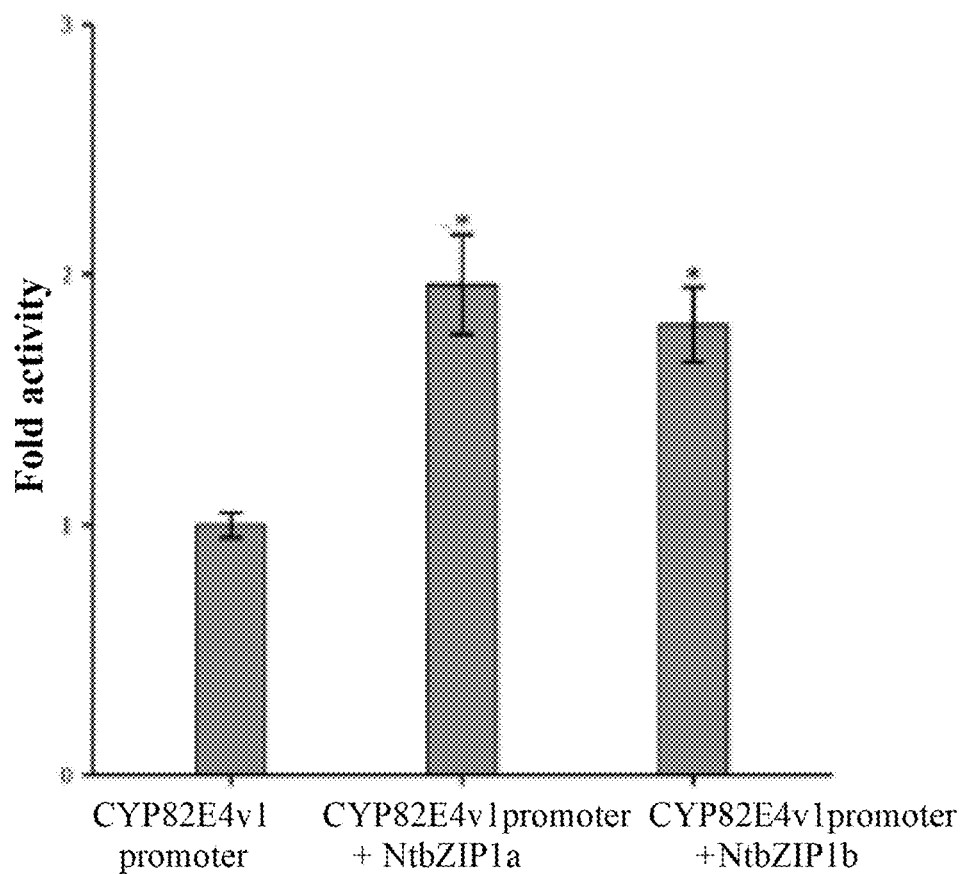
FIG. 10 shows a graph illustrating that NtbZIP1a and b significantly activate CYP82E4v1 promoter in tobacco cells.
Figure 10:
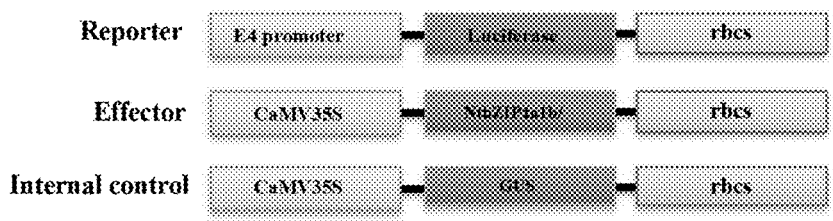

Referring to FIG. 10, the transactivation experiment was also performed using a NtbZIP1b expression vector and the E4 promoter-luciferase reporter plasmid, as described for NtbZIP1a. NtbZIP1b also activated the E4 promoter at the similar level as NtbZIP1a.

Figure 11:
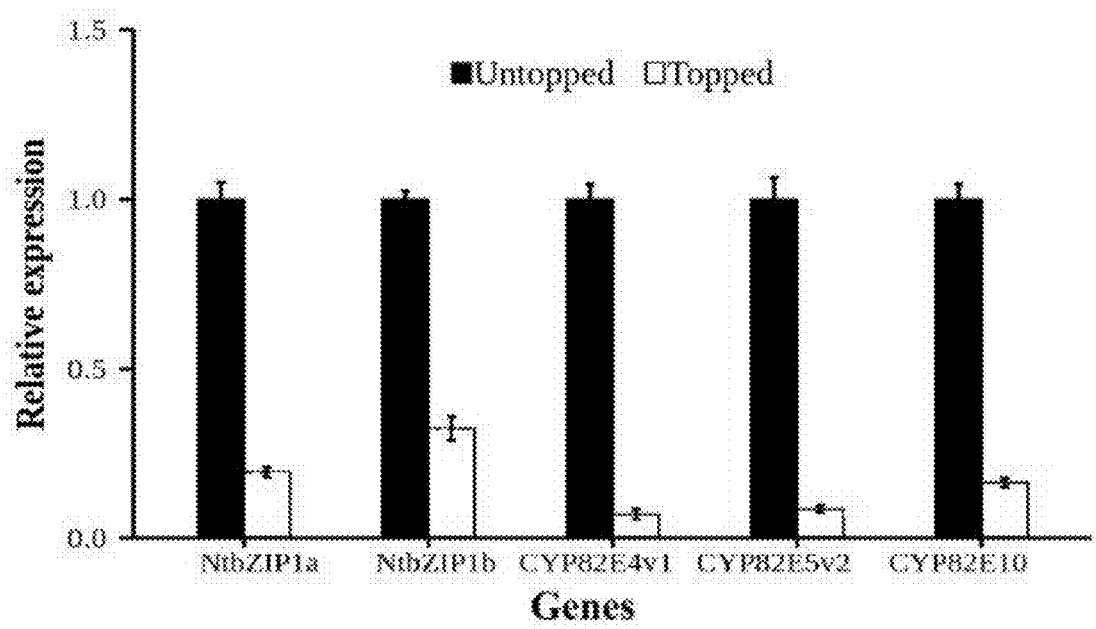
FIG. 11 shows a graph illustrating that topping of tobacco plants downregulates the expression of NtbZIPs and NNDs.

Finally, as it has been established that the agronomic practice of tobacco topping (removal of the axillary shoots) induces nicotine production, the instant inventors analyzed the transcriptome data from tobacco plants that were topped or un-topped. More specifically, leaf samples were collected after 24 hours from the control (un-topped) and topped plants. RNA isolated from un-topped and topped leaves were used for cDNA synthesis and qRT-PCR analyses. The results showed that topping resulted in decreased expression of bZIP1 a/b, as well as E4, 5, and 10, by approximately 70-90%, compared to the un-topped plants, suggesting that topping negatively regulates the expression of bZIP1 a/b and NNDs in tobacco (FIG. 11). The result also indicates that bZIP1 a/b and NNDs are coordinately expressed in tobacco, as gene regulators and their target genes usually do.

Based upon the Example above, NtbZIP1a and 1b are believed to be involved in the regulation of the three NND genes as activators. Reduction or inactivation of NtbZIP1a/b may lead to reduction of nornicotine.

Example 3

This Example describes the formation of transgenic lines overexpressing NtbZIP1a and the effect of these transgenic lines on endogenous E4 expression.

Figure 12A:
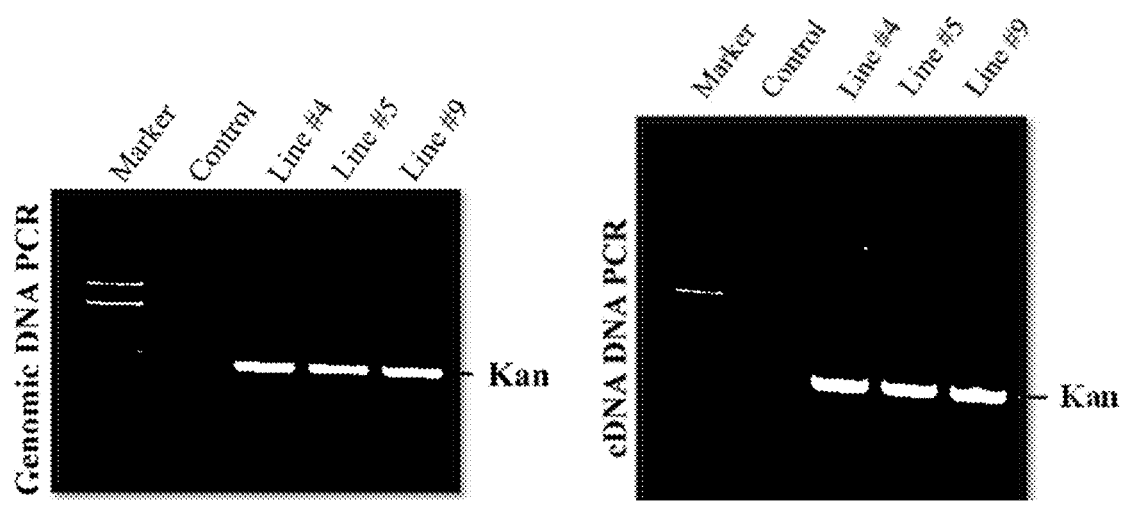
FIGS. 12A-C show graphs and images illustrating overexpression of NtbZIP1a in tobacco plants. (A) Genomic DNA PCR and cDNA PCR of control and three transgenic lines (line #4, 5, and 9) confirming the integration and expression, respectively, of the antibiotic selection marker, neomycin phosphotransferase II (npt II; Kan). (B) Quantitative real-time (qRT-PCR) analysis showing the relative expression of NtbZIP1 and E4 in control (EV) and transgenic lines (line #4, 5, and 9). (C) Metabolic analysis showing conversion of nicotine to nornicotine in control and transgenic lines ($T_0$ or first generation transgenic plants).
Figure 12B:
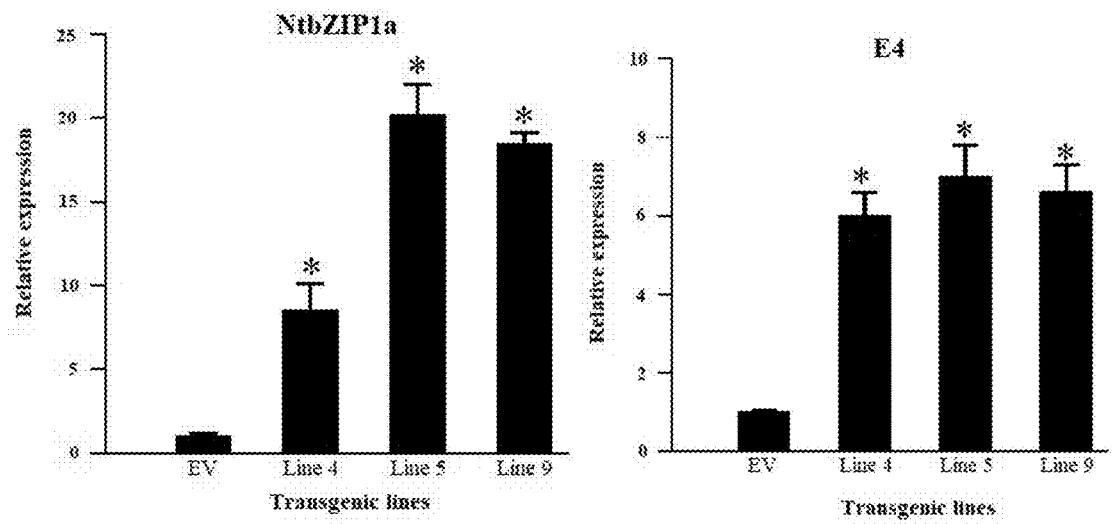

To form the transgenic lines, the pCAMBIA2300 (binary vector), containing NtbZIP1a under the control of the CaMV35S promoter and rbcS terminator, was mobilized into Agrobacterium, and tobacco leaf discs were infected with the transformed Agrobacterium. More than 20 transgenic lines overexpressing NtbZIP1a were generated from Agrobacterium-infected leaf discs. Genomic DNA isolated from control and three transgenic lines were used to verify the transgenic status of the plants by PCR amplification of the antibiotic selection marker, neomycin phophotransferase II (nptII; kan). Total RNA isolated from leaves of control and three transgenic lines were used for cDNA synthesis. RT-PCR was used to verify the expression of nptII (kan) gene in the transgenic plants (FIG. 12A). Real-time quantitative PCR (qRT-PCR) was used to detect the transcript levels of NtbZIP1a, and E4 (FIG. 12B). An ubiquitously expressed house-keeping gene, tubulin, was used as internal control in qRT-PCR.

Figure 12C:
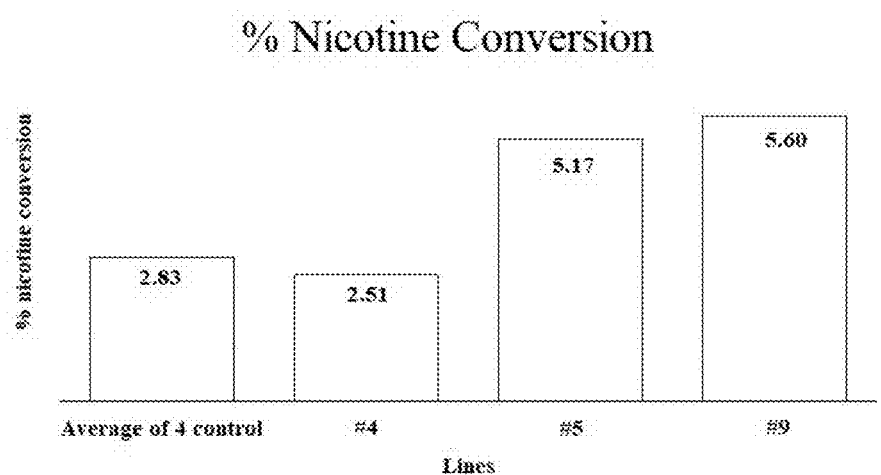

The results of this Example showed that NtbZIP1a expression was significantly higher in the transgenic plants compared with control. When NtbZIP1a was highly expressed the endogenous E4 expression was upregulated (approx. 6-8 fold), indicating that NtbZIP1a induces the expression of E4 and therefore is a possible transcriptional activator for E4 gene. Additionally, metabolic analysis shows that nicotine to nornicotine conversion is higher in transgenic tobacco leaves as compared with a control (FIG. 12C). The formula used for calculating the conversion of nicotine to nornicotine was:

$$\text{Nicotine conversion} = \frac{\text{Nornicotine}}{\text{Nicotine} + \text{Nornicotine}} \times 100$$

Two of the three lines analyzes showed higher nicotine to nornicotine conversion. Because the metabolic analysis was performed with independent $T_0$ (first generation transgenic plants) segregating population, the metabolic outcomes can vary.

Example 4

Figure 13:
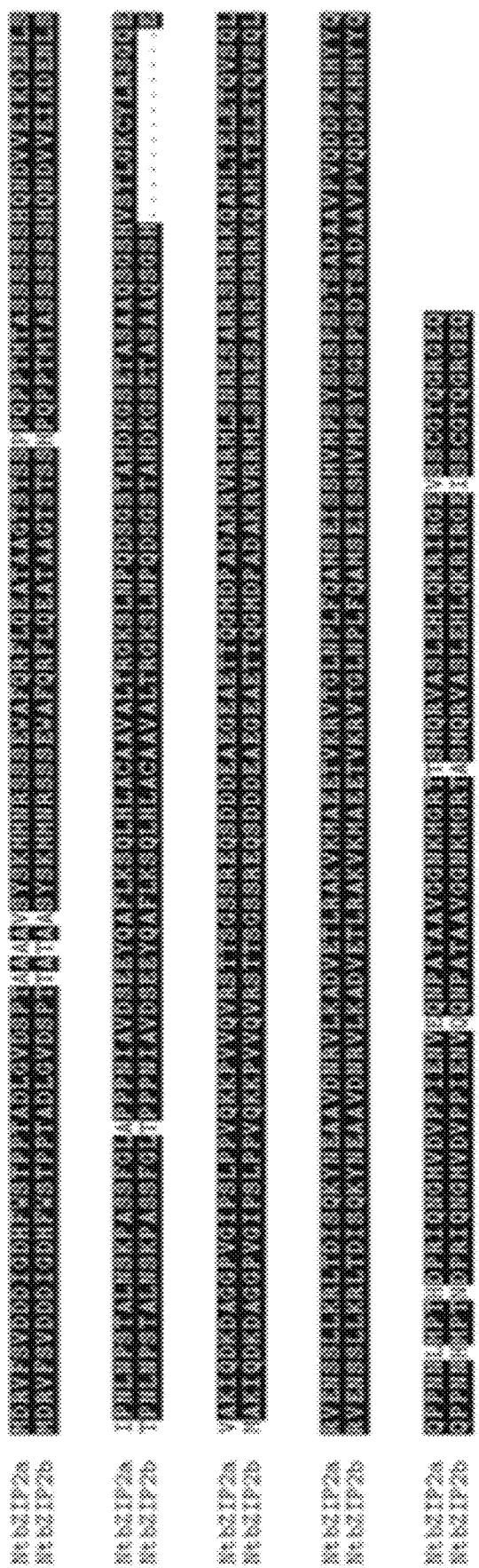
FIG. 13 shows an image illustrating amino acid sequence alignment of NtbZIP2a and 2b.

As described in Example 2 above, the instant inventors have characterized NtbZIP1a and b, two NtbZIP belonging to group S bZIP factors. In *Arabidopsis*, group S bZIP factors are known to interact with certain group C factors to regulate gene expression. In view of this interaction, the instant inventors identified the tobacco homologs of *Arabidopsis* bZIP 63, a group C member that interacts with group S factors. In tobacco, there are two bZIP 63 homologs, termed here as NtbZIP2a and b, that share greater than 95% in amino acid identity (FIG. 13). Without wishing to be bound by theory, it is believed that NtbZIP2a and b are originated from the two tobacco progenitors, *N. sylvestris* and *N. tometosiformis*, and functionally redundant.

Figure 14:
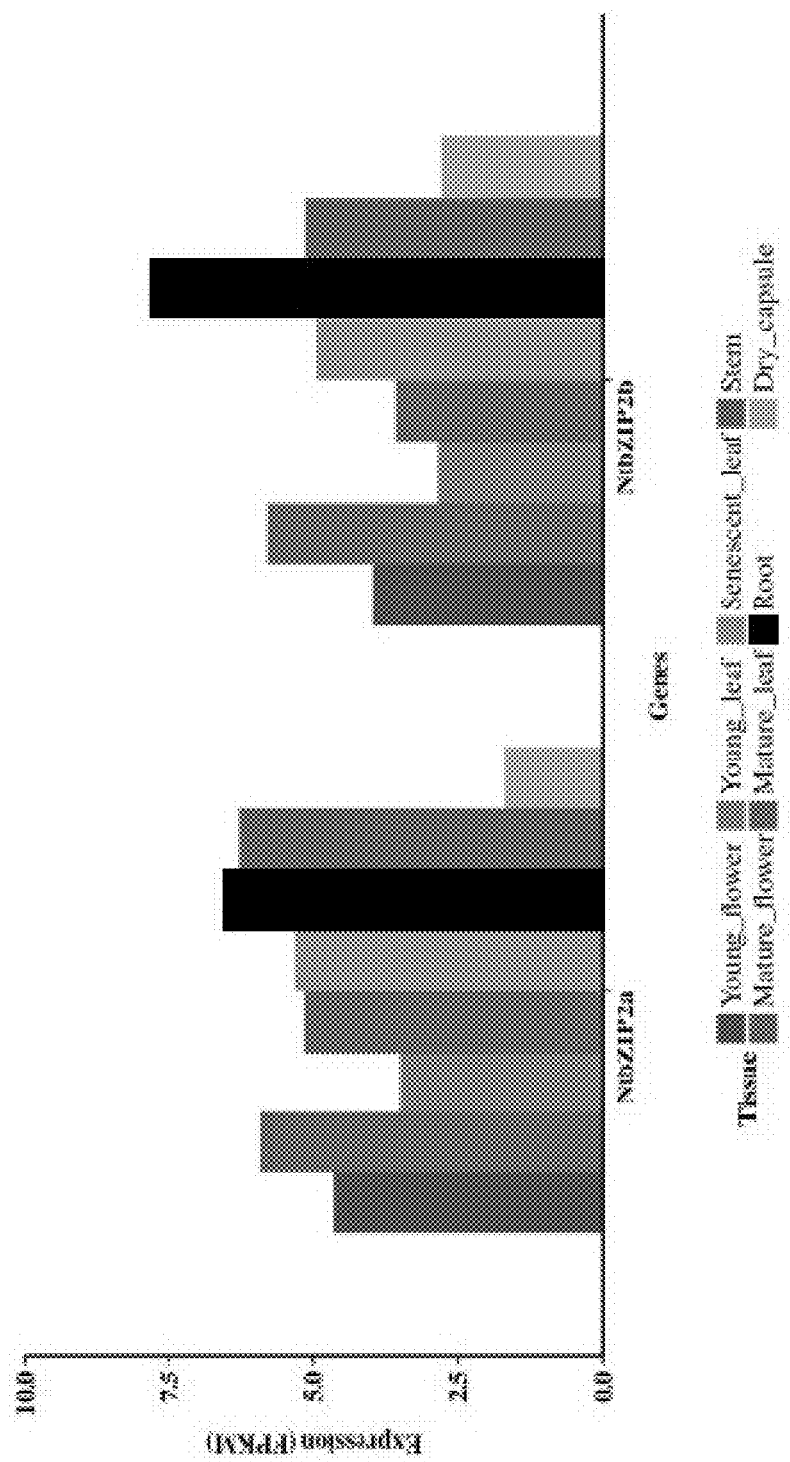
FIG. 14 shows a graph illustrating that NtbZIP2a and b have similar expression patterns in tobacco tissues.
Figure 15:
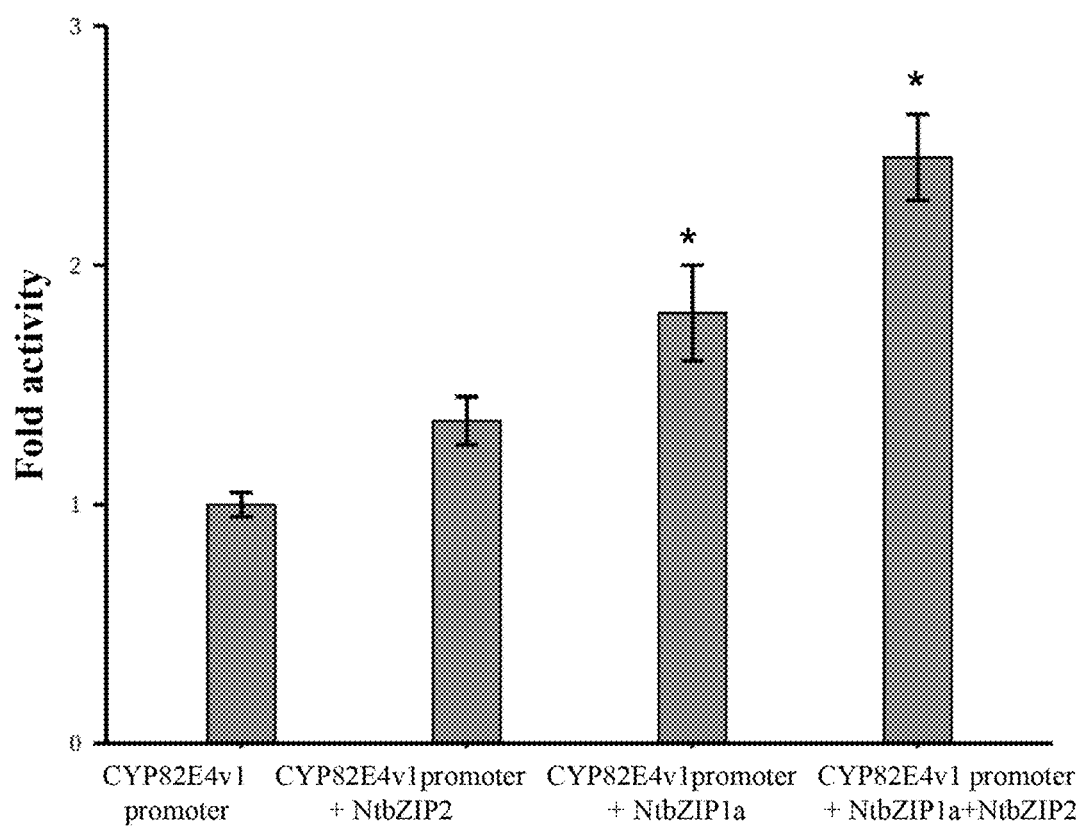
FIG. 15 shows a graph illustrating that NtbZIP2 acts synergistically with NtbZIP1 to activate the E4 promoter in tobacco cells.
Figure 15:
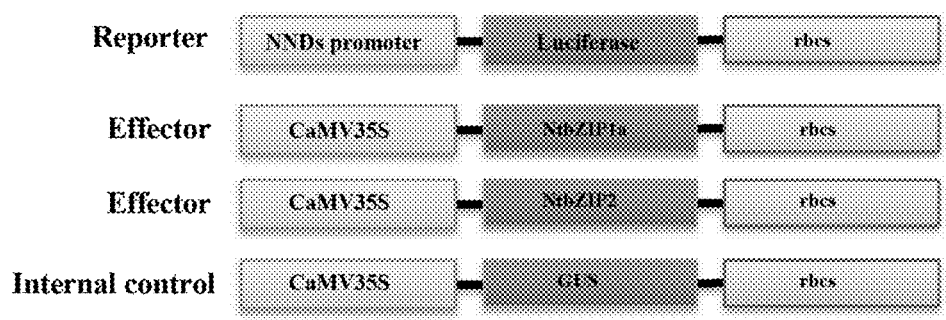

According to transcriptomic analysis, NtbZIP2a and b have similar expression patterns in tobacco flowers, leaves, stems, and roots (FIG. 14). Based upon the foregoing discussion, the instant inventors hypothesized that NtbZIP2a and b also regulate E4/5/10, individually and/or cooperatively with NtbZIP1a and b. Thus, NtbZIP2a was tested for transactivation of the E4 promoter, individually or in combination with NtbZIP1a. More specifically, the E4 promoter was fused to the firefly luciferase reporter gene and the bZIP TFs were cloned into pBS vector under the control of the CaMV 35S promoter and rbcs terminator. The results showed that, individually, both NtbZIP1a and NtbZIP2a activate the E4 promoter; however, when both NtbZIP1a and 2a were co-expressed, transactivation of the E4 promoter was significantly increased, compared to that was induced by each factor alone (FIG. 15).

Figure 16A:
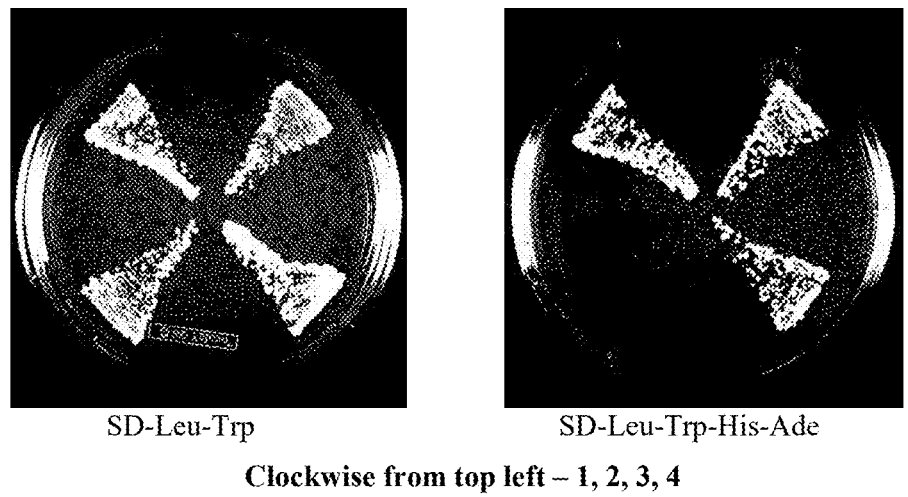
FIGS. 16A-B show images illustrating protein-protein interaction of NtbZIP1 and NtbZIP2 using yeast two hybrid assay. (A) Yeast two hybrid assay showing protein-protein interaction between NtbZIP1 and NtbZIP2. Colony growth on synthetic drop-out (SD) medium lacking leucine, tryptophan, histidine and adenine (-leu-trp-his-ade) indicates interaction between the proteins (bZIPs). (B) Schematic diagram of NtbZIP1 and NtbZIP2. The bZIP domain is indicated by "shaded" rectangle. The numbers indicate the amino acid.
Figure 16B:
Figure 16B:

Next, to determine whether NtbZIP1a/b interact with NtbZIP2a, the inventors performed yeast hybrid assay. The growth of the yeast cells on synthetic drop-out (SD) medium lacking leucine, trptophan, histidine, and adenine (SD-leu-trp-his-ade) suggests that NtbZIP1a/b interact with NtbZIP2a (FIG. 16A; 1 and 2). In addition, NtbZIP2 interacts with itself to form a homo-dimer (FIG. 16A; 3). The bZIP domains of NtbZIP1 and NtbZIP2 are illustrated in FIG. 16B.

Although the instant Example only tested NtbZIP2a activity on the E4 promoter, but not the E5 or E10 promoters, it is believed that both NtbZIP2 factors are activators of E4/5/10 genes. That is, this Example suggests that the group C NtbZIP2a and b are two previously uncharacterized regulators of E4/5/10 genes. In addition, this Example shows that NtbZIP1 and NtbZIP2 are synergistic in activation of the E4 (possibly E5 and 10) promoter. In particular, without wishing to be bound by theory, it is believed that NtbZIP2a and/or b interact with NtbZIP1a and/or b to enhance DNA binding ability and significantly increase activation of the E4/5/10 promoters, as compared to NtbZIP1 or NtbZIP2 alone.

In summary, two group S and two group C NtbZIP factors that are positive regulators of E4/5/10 genes were characterized herein. The transactivation activities of NtbZIP1a and 2a on the E4 promoter are additive. Therefore, without wishing to be bound by theory, it is believed that knockout approaches to inactivate one or all of these genes reduces E4/5/10 gene expression.

Example 5

NtbZIP1 RNAi lines were generated (tobacco cultivar Samsun NN) and molecular and biochemical analysis was performed.

Figure 17:
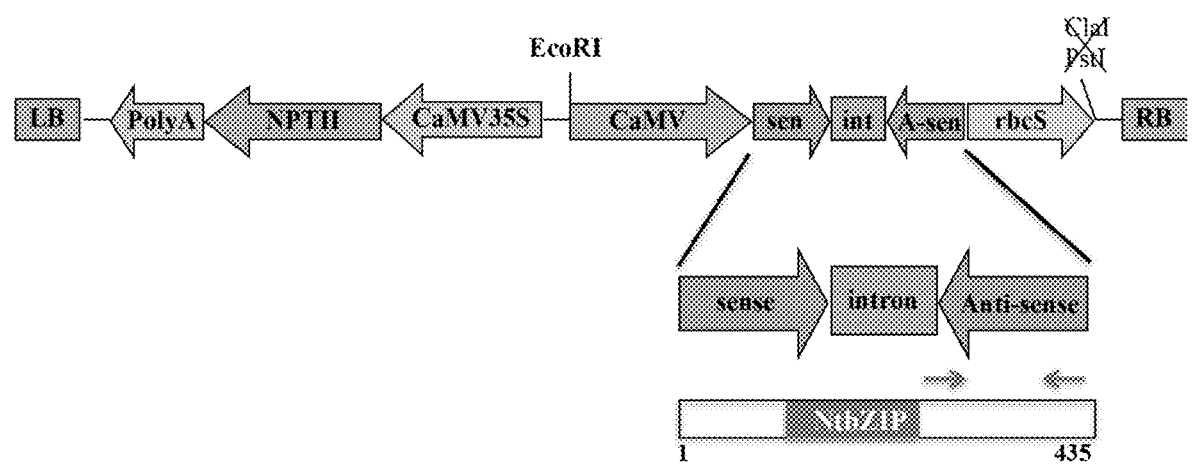
FIG. 17 includes a schematic diagram of the RNAi vector containing a part of the tobacco bZIP1 both in sense and anti-sense orientation with an intron. The partial cDNA with the intron is expressed under the control of the CaMV 35S promoter and rbcS terminator. RNAi primers (indicated by arrowheads) are designed to amplify the sequences outside of the conserved domain.

An RNAi vector was construction and plants were transformed. For construction of the RNAi plasmid, a 200 bp fragment from 3' end of the NtbZIP1a cDNA was PCR amplified and cloned in sense and antisense orientations into the pKYLX80 vector containing an intron (from the soybean FADS gene; Schardl et al. 1987). The sense and antisense fragments with the intron were excised from pKYLX80 and cloned into binary vector pCAMBIA2300 containing the CaMV35S promoter and rbcS terminator (FIG. 17). The plasmid was mobilized into *Agrobacterium tumefasiens* by a freeze-thaw method (Weigel and Glazebrook, 2006). Tobacco plants (*N. tabacum* cv. Samsun NN) were transformed with the *Agrobacterium* harboring the binary vector as described previously (Pattanaik et al. 2008) and two independent kanamycin-resistant transgenic lines (line #3 and 9) were selected for further analysis.

Figure 18A:
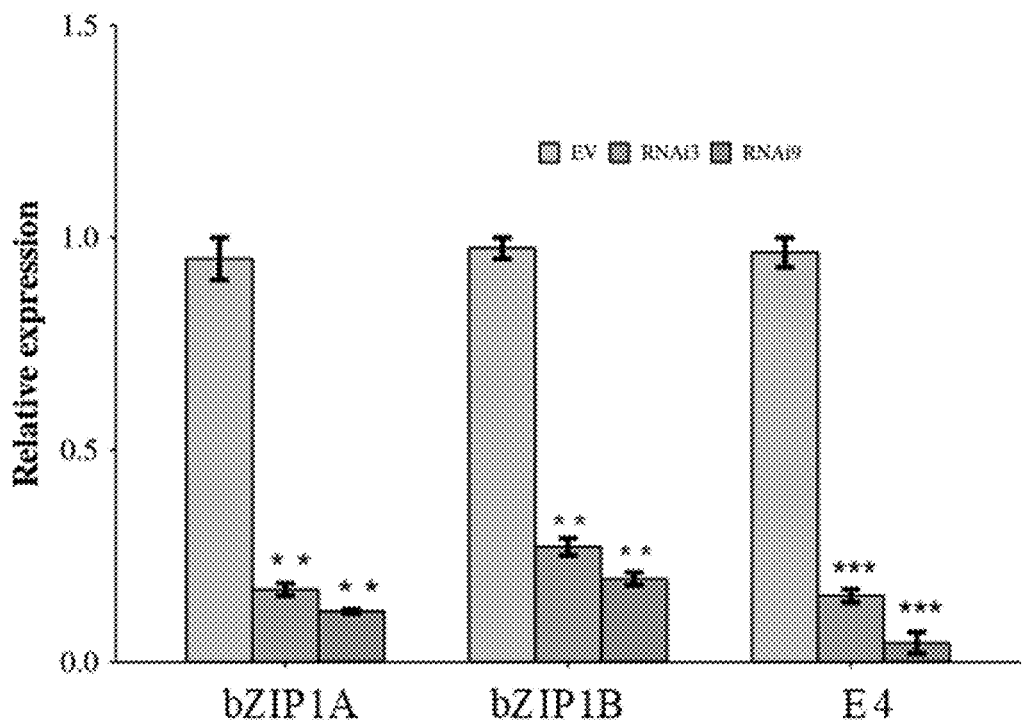
FIG. 18A-B illustrates (A) expression of NtbZIP1a and NtbZIP1b were reduced by 70-80% and E4 by 80-90% in RNAi lines compared to EV control. (B) Nicotine-to-nornicotine conversion was down by approximately 50% in RNAi lines compared to EV plants.
Figure 18B:
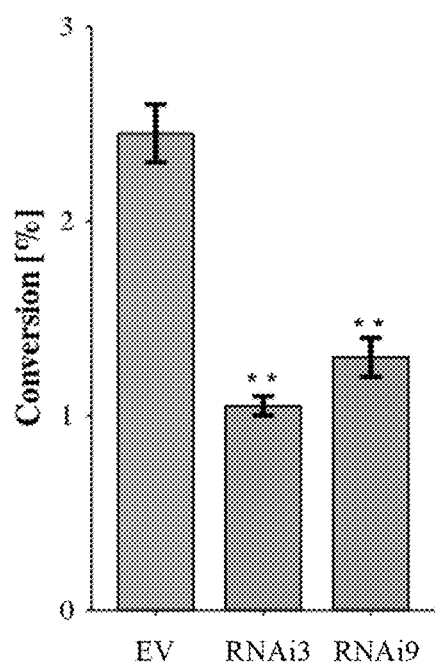

RNA isolated from leaves of NtbZIP RNAi and empty vector (EV) control plants were used for cDNA synthesis and quantitative RT-PCR (qPCR). Expression of NtbZIP1a in two independent RNAi lines was reduced by approximately 80% compared to the EV line (FIG. 18A). In addition, NtbZIP1b expression was reduced by approximately 70% in the two RNAi lines compared to EV (FIG. 18A). Expression of E4 was significantly reduced in the two transgenic lines, e.g. up to 90% reduction in line 9 (FIG. 18A). The results indicate that repression of NtbZIP1 leads to downregulation of E4, suggesting NtbZIP1a and NtbZIP1b regulate E4 gene. In addition, the nicotine-to-nornicotine conversion was measured in leaves of RNAi and EV lines. Nicotine-to-nornicotine conversion was reduced by approximately 50% in RNAi lines compared to EV lines (FIG. 18B).

To summarize, RNAi-mediated silencing of NtbZIP1 significantly reduces the expression of E4 in transgenic tobacco plants compared to EV. In addition, nicotine-to-nornicotine conversion is approximately 50% lower in leaves of the transgenic RNAi tobacco compared with EV.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

[1] Gavilano, L. B., and Siminszky, B. (2007). Isolation and characterization of the cytochrome P450 gene CYP82E5v2 that mediates nicotine to nornicotine conversion in the green leaves of tobacco. Plant & cell physiology 48, 1567-1574.

[2] Higo, K., Ugawa, Y., Iwamoto, M., and Higo, H. (1998). PLACE: a database of plant cis-acting regulatory DNA elements. Nucleic acids research 26, 358-359.

[3] Leitch, I. J., Hanson, L., Lim, K. Y., Kovarik, A., Chase, M. W., Clarkson, J. J., and Leitch, A. R. (2008). The ups and downs of genome size evolution in polyploid species of *Nicotiana* (Solanaceae). Annals of botany 101, 805-814.

[4] Lescot, M., Dehais, P., Thijs, G., Marchal, K., Moreau, Y., Van de Peer, Y., Rouze, P., and Rombauts, S. (2002). PlantCARE, a database of plant cis-acting regulatory elements and a portal to tools for in silico analysis of promoter sequences. Nucleic acids research 30, 325-327.

[5] Lewis, R. S., Bowen, S. W., Keogh, M. R., and Dewey, R. E. (2010). Three nicotine demethylase genes mediate nornicotine biosynthesis in *Nicotiana tabacum* L.: functional characterization of the CYP82E10 gene. Phytochemistry 71, 1988-1998.

[6] Lim, K. Y., Matyasek, R., Kovarik, A., and Leitch, A. R. (2004). Genome evolution in allotetraploid *Nicotiana*. Biol J. Linn Soc 82, 599-606.

[7] Morita, M., Shitan, N., Sawada, K., Van Montagu, M. C., Inze, D., Rischer, H., Goossens, A., Oksman-Caldentey, K. M., Moriyama, Y., and Yazaki, K. (2009). Vacuolar transport of nicotine is mediated by a multidrug and toxic compound extrusion (MATE) transporter in *Nicotiana tabacum*. Proceedings of the National Academy of Sciences of the United States of America 106, 2447-2452.

[8] Pattanaik, S., Werkman, J. R., Kong, Q., and Yuan, L. (2010a). Site-directed mutagenesis and saturation mutagenesis for the functional study of transcription factors involved in plant secondary metabolite biosynthesis. Methods in molecular biology 643, 47-57.

[9] Pattanaik, S., Kong, Q., Zaitlin, D., Werkman, J. R., Xie, C. H., Patra, B., and Yuan, L. (2010b). Isolation and functional characterization of a floral tissue-specific R2R3 MYB regulator from tobacco. Planta 231, 1061-1076.

[10] Shoji, T., and Hashimoto, T. (2011). Tobacco MYC2 regulates jasmonate-inducible nicotine biosynthesis genes directly and by way of the NIC2-locus ERF genes. Plant & cell physiology 52, 1117-1130.

[11] Shoji, T., Kajikawa, M., and Hashimoto, T. (2010). Clustered transcription factor genes regulate nicotine biosynthesis in tobacco. The Plant cell 22, 3390-3409.

[12] Shoji, T., Inai, K., Yazaki, Y., Sato, Y., Takase, H., Shitan, N., Yazaki, K., Goto, Y., Toyooka, K., Matsuoka, K., and Hashimoto, T. (2009). Multidrug and toxic compound extrusion-type transporters implicated in vacuolar sequestration of nicotine in tobacco roots. Plant physiology 149, 708-718.

[13] Sierro, N., van Oeveren, J., van Eijk, M. J., Martin, F., Stormo, K. E., Peitsch, M. C., and Ivanov, N. V. (2013a).

Whole genome profiling physical map and ancestral annotation of tobacco Hicks Broadleaf. The Plant journal: for cell and molecular biology 75, 880-889.

[14] Sierro, N., Battey, J. N., Ouadi, S., Bovet, L., Goepfert, S., Bakaher, N., Peitsch, M. C., and Ivanov, N. V. (2013b). Reference genomes and transcriptomes of *Nicotiana sylvestris* and *Nicotiana tomentosiformis*. Genome biology 14, R60.

[15] Sierro, N., Battey, J. N., Ouadi, S., Bakaher, N., Bovet, L., Willig, A., Goepfert, S., Peitsch, M. C., and Ivanov, N. V. (2014). The tobacco genome sequence and its comparison with those of tomato and potato. Nature communications 5, 3833.

[16] Siminszky, B., Gavilano, L., Bowen, S. W., and Dewey, R. E. (2005). Conversion of nicotine to nornicotine in *Nicotiana tabacum* is mediated by CYP82E4, a cytochrome P450 monooxygenase. Proceedings of the National Academy of Sciences of the United States of America 102, 14919-14924.

[17] Singh, S. K., Wu, Y., Ghosh, J. S., Pattanaik, S., Fisher, C., Wang, Y., Lawson, D., and Yuan, L. (2015). RNA-sequencing Reveals Global Transcriptomic Changes in *Nicotiana tabacum* Responding to Topping and Treatment of Axillary-shoot Control Chemicals. Scientific reports 5, 18148.

[18] Van Moerkercke, A., Steensma, P., Schweizer, F., Pollier, J., Gariboldi, I., Payne, R., Vanden Bossche, R., Miettinen, K., Espoz, J., Purnama, P. C., Kellner, F., Seppanen-Laakso, T., O'Connor, S. E., Rischer, H., Memelink, J., and Goossens, A. (2015). The bHLH transcription factor BIS1 controls the iridoid branch of the monoterpenoid indole alkaloid pathway in *Catharanthus roseus*. Proceedings of the National Academy of Sciences of the United States of America 112, 8130-8135.

[19] Yu, F., and De Luca, V. (2013). ATP-binding cassette transporter controls leaf surface secretion of anticancer drug components in *Catharanthus roseus*. Proceedings of the National Academy of Sciences of the United States of America 110, 15830-15835.

[20] Ehlert, A., et al. (2006) Two-hybrid protein—protein interaction analysis in *Arabidopsis* protoplasts: establishment of a heterodimerization map of group C and group S bZIP transcription factors. The Plant Journal, 46: 890-900.

[21] Pattanaik S, Xie C H, Yuan L (2008) The interaction domains of the plant Myc-like bHLH transcription factors can regulate the transactivation strength. Planta 227:707-715.

[22] Schardl C L, Byrd A D, Benzion G, Altschuler M A, Hildebrand D F, Hunt A G (1987) Design and construction of a versatile system for the expression of foreign genes in plants. Gene 61: 1-11.

[23] Weigel D, Glazebrook J (2006) Transformation of *Agrobacterium* using the freeze-thaw method. Cold Spring Harbor Protocols 2006: Pdb.prot4666.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

What is claimed is:

1. A method of decreasing conversion of nicotine to nornicotine and/or a method of reducing levels of at least one tobacco specific (TSNA) precursor, the method comprising
reducing the activity and/or expression of at least one basic region/leucine zipper (bZIP) type transcription factor in a tobacco plant, a part of a tobacco plant, a tobacco plant cell or cell culture, or a tobacco plant seed, wherein the bZIP transcription factor comprises
an amino acid sequence encoded by the nucleic acid sequence of SEQ ID NO: 1 or 3;
an amino acid having the sequence of SEQ ID NO: 2, 4, 5, or 6;
an amino acid sequence having at least 95% identity to the amino acid sequence encoded by the nucleic acid sequence of SEQ ID NO: 1 or 3 and which binds a promoter of a nicotine N-demethylase (NND) selected from the group consisting of CYP82E4v1, CYP82E5v2, and CYP82E10;
an amino acid sequence having at least 95% identity to the amino acid sequence of SEQ ID NO: 2, 4, 5, or 6 and which binds a promoter of a nicotine N-demethylase (NND) selected from the group consisting of CYP82E4v1, CYP82E5v2, and CYP82E10; or combinations thereof.

2. The method of claim 1, wherein the at least one bZIP transcription factor is selected from the group consisting of group C bZIP transcription factor, group S bZIP transcription factor, and combinations thereof.

3. The method of claim 1, wherein the at least one bZIP transcription factor is selected from the group consisting of NtbZIP1a, NtbZIP1b, NtbZIP2a, NtbZIP2b, and combinations thereof.

4. The method of claim 1, wherein the at least one bZIP transcription factor comprises an amino acid molecule having at least 97%, 98%, 99%, or 100% identity to an amino acid selected from the group consisting of the amino acid encoded by SEQ ID NO: 1; the amino acid of SEQ ID NO: 2; the amino acid encoded by SEQ ID NO: 3; the amino acid of SEQ ID NO: 4; the amino acid of SEQ ID NO: 5; and the amino acid of SEQ ID NO: 6.

5. The method of claim 1, wherein the at least one bZIP transcription factor comprises NtbZIP1a and NtbZIP1b.

6. The method of claim 1, wherein the at least one bZIP transcription factor comprises NtbZIP2a and NtbZIP2b.

7. The method of claim 1, wherein the at least one bZIP transcription factor comprises NtbZIP1a, NtbZIP1b, NtbZIP2a, and NtbZIP2b.

8. The method of claim 1, wherein the at least one bZIP transcription factor comprises:
an amino acid molecule having at least 97%, 98%, 99%, or 100% identity to an amino acid selected from the group consisting of the amino acid encoded by SEQ ID NO: 1 and the amino acid of SEQ ID NO: 2; and
an amino acid molecule having at least 97%, 98%, 99%, or 100% identity to an amino acid selected from the group consisting of the amino acid encoded by SEQ ID NO: 3 and the amino acid of SEQ ID NO: 4.

9. The method of claim 1, wherein the at least one bZIP transcription factor comprises:
an amino acid molecule having at least 97%, 98%, 99%, or 100% identity to the amino acid of SEQ ID NO: 5; and
an amino acid molecule having at least 97%, 98%, 99%, or 100% identity to the amino acid of SEQ ID NO: 6.

10. The method of claim 1, wherein the at least one bZIP transcription factor comprises:
an amino acid molecule having at least 97%, 98%, 99%, or 100% identity to an amino acid selected from the group consisting of the amino acid encoded by SEQ ID NO: 1 and the amino acid of SEQ ID NO: 2;
an amino acid molecule having at least 97%, 98%, 99%, or 100% identity to an amino acid selected from the group consisting of the amino acid encoded by SEQ ID NO: 3 and the amino acid of SEQ ID NO: 4;
an amino acid molecule having at least 97%, 98%, 99%, or 100% identity to the amino acid of SEQ ID NO: 5; and/or
an amino acid molecule having at least 97%, 98%, 99%, or 100% identity to the amino acid of SEQ ID NO: 6.

11. The method of claim 1, wherein reducing the activity and/or expression of the at least one bZIP type transcription factor comprises: mutating the bZIP type transcription factor by providing a mutation in a binding site of the bZIP type transcription factor; mutating the binding site on a promoter of a nicotine N-demethylase (NND); using a bZIP type transcription factor inhibitor; or using a gene silencing technique.

12. The method of claim 11, wherein the bZIP transcription factor inhibitor is selected from the group consisting of antisense oligonucleotides, miRNA, siRNA, locked nucleic acid (LNA) nucleotides, and combination thereof.

13. The method of claim 11, wherein mutating the bZIP type transcription factor comprises mutating the binding site on a promoter of a nicotine N-demethylase (NND).

14. The method of claim 13, wherein the NND is selected from the group consisting of CYP82E4v1, CYP82E5v2, and CYP82E10.

15. The method of claim 14, wherein the NND is CYP82E4v1 and wherein the bZIP binding site on the promoter of CYP82E4v1 is an A/G box with a pre-mutated sequence of TACGTC.

16. The method of claim 15, wherein the mutated binding site has the sequence TGCGTC.

17. The method of claim 16, wherein the mutated binding site is formed by site-directed mutagenesis.

18. The method of claim 11, wherein mutating the bZIP type transcription factor comprises mutating a plant genome to knockout at least one basic region/leucine zipper (bZIP) type transcription factor.

19. The method of claim 18, wherein the at least one bZIP transcription factor is selected from the group consisting of group C bZIP transcription factor, group S bZIP transcription factor, and combinations thereof.

20. The method of claim 18, wherein the at least one bZIP transcription factor is selected from the group consisting of NtbZIP1a, NtbZIP1b, NtbZIP2a, NtbZIP2b, and combinations thereof.

21. The method of claim 18, wherein the at least one bZIP transcription factor comprises an amino acid sequence selected from the group consisting of:
an amino acid molecule having at least 97%, 98%, 99%, or 100% identity to an amino acid selected from the group consisting of the amino acid encoded by SEQ ID NO: 1 and the amino acid of SEQ ID NO: 2;
an amino acid molecule having at least 97%, 98%, 99%, or 100% identity to an amino acid selected from the group consisting of the amino acid encoded by SEQ ID NO: 3 and the amino acid of SEQ ID NO: 4;
an amino acid molecule having at least 97%, 98%, 99%, or 100% identity to the amino acid of SEQ ID NO: 5; and
an amino acid molecule having at least 97%, 98%, 99%, or 100% identity to the amino acid of SEQ ID NO: 6.

22. A tobacco cell culture or plant:
comprising a plant cell comprising a nucleic acid molecule encoding a bZIP type transcription factor having at least one mutation, wherein the bZIP transcription factor comprises an amino acid sequence encoded by the nucleic acid sequence of SEQ ID NO: 1 or 3; an amino acid having the sequence of SEQ ID NO: 2, 4, 5, or 6; or combinations thereof;
wherein the tobacco cell culture or plant provides a decrease in conversion of nicotine to nornicotine and/or reduction in levels of at least one tobacco specific (TSNA) precursor of said culture or plant compared with that of an unmodified culture or plant.

23. A method of breeding a tobacco plant, the method comprising breeding the tobacco cell culture or plant of claim 22.

24. A method of producing a tobacco industry product, the method comprising producing the tobacco cell culture or plant of claim 22.

25. A method of growing a crop, the method comprising growing the tobacco cell culture or plant of claim 22.

26. A method of producing a processed tobacco leaf, the method comprising processing the tobacco cell culture or plant of claim 22.

27. The method of claim 26, where the processed tobacco leaf is a cured tobacco leaf.

28. A harvested leaf of a tobacco plant according to claim 22.

29. The harvested leaf according to claim 28, wherein the leaf is a cut harvested leaf.

30. A processed tobacco leaf comprising a plant cell comprising a nucleic acid molecule encoding a bZIP type transcription factor having at least one mutation, wherein the bZIP transcription factor comprises an amino acid sequence encoded by the nucleic acid sequence of SEQ ID NO: 1 or 3; an amino acid having the sequence of SEQ ID NO: 2, 4, 5, or 6; or combinations thereof, wherein the leaf is a non-viable processed tobacco leaf.

31. A processed tobacco leaf comprising a plant cell comprising a nucleic acid molecule encoding a bZIP type transcription factor having at least one mutation, wherein the bZIP transcription factor comprises an amino acid sequence encoded by the nucleic acid sequence of SEQ ID NO: 1 or 3; an amino acid having the sequence of SEQ ID NO: 2, 4, 5, or 6; or combinations thereof, wherein the plant or leaf is processed by curing, fermentation, pasteurizing or combinations thereof.

32. A processed tobacco leaf comprising a plant cell comprising a nucleic acid molecule encoding a bZIP type transcription factor having at least one mutation, wherein the bZIP transcription factor comprises an amino acid sequence encoded by the nucleic acid sequence of SEQ ID NO: 1 or 3; an amino acid having the sequence of SEQ ID NO: 2, 4, 5, or 6; or combinations thereof, wherein the processed tobacco leaf is a cut processed tobacco leaf.

33. Cured tobacco material made from a plant, a part thereof, an extract thereof, or a cell culture comprising a plant cell comprising a nucleic acid molecule encoding a bZIP type transcription factor having at least one mutation, wherein the bZIP transcription factor comprises an amino acid sequence encoded by the nucleic acid sequence of SEQ ID NO: 1 or 3; an amino acid having the sequence of SEQ ID NO: 2, 4, 5, or 6; or combinations thereof.

34. A tobacco blend comprising the cured tobacco material of claim 33.

35. A tobacco industry product prepared from a tobacco plant according to claim 22, a part thereof, or a plant extract obtained therefrom.

36. The tobacco industry product according to claim 35, wherein the tobacco industry product is a smoking article.

37. The tobacco industry product according to claim 35, wherein the tobacco industry product is a smokeless tobacco product.

38. The tobacco industry product according to claim 35, wherein the tobacco product is a non-combustible aerosol provision system such as a tobacco heating device, e.g. an aerosol-generating device.

39. A combustible smoking article, non-combustible aerosol provisioning system, smokeless tobacco product, or tobacco heating comprising a plant or a portion thereof from the species *Nicotiana tabacum* according to claim 22 or an extract thereof or a tobacco cell culture according to claim 22 or a cured tobacco material according to claim 33 or a tobacco blend according to claim 34.

40. The tobacco cell culture or plant of claim 22, wherein the bZIP transcription factor comprises NtbZIP1a, NtbZIP1b, NtbZIP2a, NtbZIP2b, or combinations thereof.

* * * * *